United States Patent
Akatsuka et al.

(10) Patent No.: US 6,660,143 B1
(45) Date of Patent: Dec. 9, 2003

(54) OXYGEN SENSOR

(75) Inventors: Shoji Akatsuka, Aichi (JP); Satoshi Ishikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/590,142

(22) Filed: Jun. 9, 2000

(30) Foreign Application Priority Data

Jun. 11, 1999 (JP) ............................................. 11-165819
Feb. 22, 2000 (JP) ....................................... 2000-044836

(51) Int. Cl.[7] ........................................... G01N 27/407
(52) U.S. Cl. ...................... 204/424; 204/408; 204/427; 204/428; 205/785
(58) Field of Search ................................ 204/421–429, 204/408; 205/785

(56) References Cited

U.S. PATENT DOCUMENTS

| 4,741,816 A | 5/1988 | Nishio et al. |
| 4,944,861 A | * 7/1990 | Reber |
| 5,573,650 A | * 11/1996 | Fukaya et al. |
| 5,759,365 A | 6/1998 | Yamada et al. |
| 5,804,050 A | 9/1998 | Hayakawa et al. |
| 5,900,129 A | * 5/1999 | Tsuji et al. |

FOREIGN PATENT DOCUMENTS

| JP | 9-325128 | 12/1997 |
| JP | 11-44668 | 2/1999 |

OTHER PUBLICATIONS

Merriam–Webster's Collegiate Dictionary, 10th ed., (1998) month unavailable, p. 517.*

* cited by examiner

Primary Examiner—T. Tung
(74) Attorney, Agent, or Firm—Sughrue Mion, PLLC

(57) ABSTRACT

A sensor structure having a metallic terminal member. The metallic terminal member 23 includes press portions 23d and 23e, which press the heating member 3 in a direction intersecting the center axis of a hollow portion 2a of an oxygen detection element 2. Holding means for holding the heating member 3 is formed separately from the metallic terminal member 23. Thus, without use of special heating-member holder means, the metallic terminal member 23 can bring at least a portion of the heating member 3 into contact with the inner wall surface of the hollow portion 2a of the oxygen detection element 2.

15 Claims, 15 Drawing Sheets

Fig. 7 (a)
Fig. 7 (b)
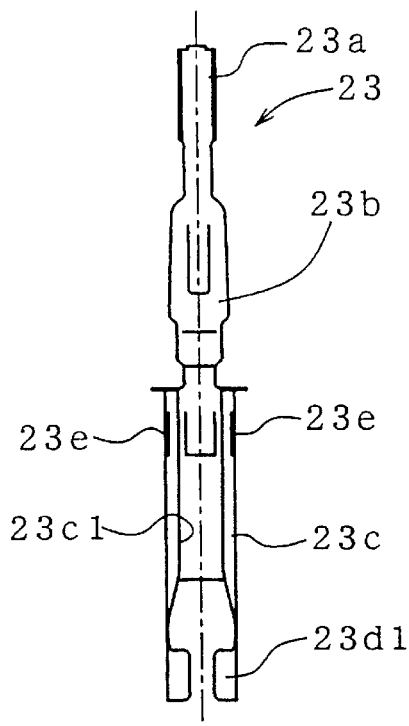
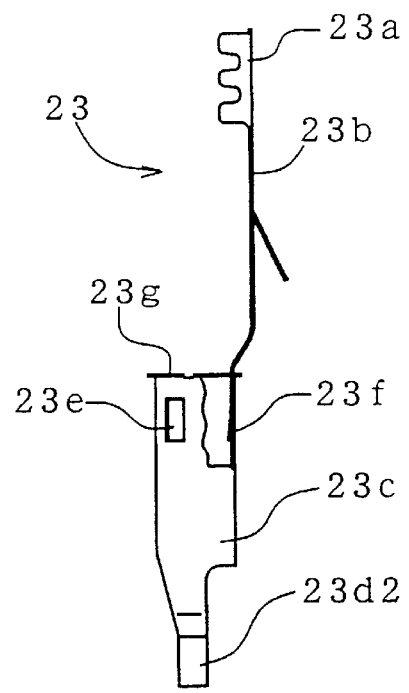
Fig. 7 (c)

DETAIL OF X PORTION

INSERTING DIRECTION OF HEATING MEMBER 3

DETAIL OF Y PORTION

INSERTING DIRECTION OF HEATING MEMBER 3

DETAIL OF Z PORTION

INSERTING DIRECTION OF HEATING MEMBER 3

DETAILED SECTION OF Z PORTION

A'-A'

B'-B'

C'-C'

OXYGEN SENSOR

BACKGROUND OF THE INVENTION

1. Field of the Invention

The present invention relates to an oxygen sensor for detecting oxygen in a gas to be measured, such as exhaust gas from an internal combustion engine.

2. Description of the Related Art

A known oxygen sensor includes an oxygen detection element assuming the form of a hollow rod which is closed at a front end, and having electrode layers formed on the inner and outer surfaces thereof. In an oxygen sensor of this type, while the atmosphere serving as a reference gas is introduced into an oxygen detection element such that the inner surface (internal electrode layer) of the element is exposed to the reference gas, the outer surface (external electrode layer) of the oxygen detection element is exposed to exhaust gas. As a result, an electromotive force is induced in the oxygen detection element by the oxygen concentration cell effect, according to the difference in oxygen concentration between the inner and outer surfaces. This electromotive force induced by the oxygen concentration cell effect is led out from the internal and external electrode layers through lead wires and serves as a detection signal indicative of oxygen concentration in the exhaust gas.

In an oxygen sensor of this type, when the temperature of exhaust gas is low, as is the case upon startup of an engine, an oxygen detection element formed of a solid electrolyte member is not sufficiently active, consuming a considerably long time before providing an electromotive force which is sufficiently large to be measurable. In order to cope with this problem, a rodlike heating member having a heating portion is inserted into a hollow portion of the oxygen detection element so as to activate the oxygen detection element through application of heat at the time of startup of the engine, thereby promptly rendering output (electromotive force) available for measurement at the time of startup of the engine, when exhaust gas contains a relatively large amount of harmful components.

In order to efficiently transmit to the oxygen detection element heat generated by the heating member, for improved activity of the oxygen detection element at the time of startup, the oxygen sensor may assume a structure such that the heating portion of the heating member is brought into contact with the inner wall surface of the hollow portion of the oxygen detection element. In such an oxygen sensor, a metallic terminal member—which is inserted into the hollow portion of the oxygen detection element and is electrically conductive with an internal electrode layer formed on the inner surface of the oxygen detection element—as a single or a plurality of holder portions (holder means), each having a substantially C-shaped cross section, so as to hold the heating member. Being held by means of the holder portion(s), the heating member is disposed within the oxygen detection element such that a front end portion of the heating member is in contact with the inner wall surface of the hollow portion of the oxygen detection element. In order to hold the heating member firmly and to maintain the end portion of the heating member in contact with the inner wall surface of the hollow portion of the oxygen detection element, the metallic terminal member including the holder portion(s) assumes a complicated form which requires bending in the course of manufacture thereof. Further, assembly of the oxygen sensor requires a jig for preliminarily attaching the heating member to the metallic terminal member. These features increase the cost of manufacture of the oxygen sensor.

SUMMARY OF THE INVENTION

It is therefore an object of the present invention to provide a sensor structure which does not require attachment of special heating-member holder means to a metallic terminal member and which allows for simple assembly.

To achieve the above object, an oxygen sensor according to a first aspect of the invention is characterized by comprising:

an oxygen detection element assuming the form of a hollow rod which is closed at a front end, and having electrode layers formed on the inner and outer surfaces of a hollow portion thereof;

a rodlike heating member disposed within the hollow portion of the oxygen detection element and adapted to heat the oxygen detection element; and a metallic terminal member formed so as to circumferentially surround the heating member and having an attachment portion, which is fixedly attached to the inner surface of the oxygen detection element, directly or indirectly via another member.

The metallic terminal member includes at least one press portion for pressing the heating member in a direction intersecting the center axis of the hollow portion of the oxygen detection element.

The heating member is held by holding means formed separately from the metallic terminal member, and the press portion causes at least a portion of the heating member to be in contact with the inner wall surface of the hollow portion of the oxygen detection element.

According to the first aspect of the invention, the metallic terminal member includes a press portion for pressing the heating member in a direction intersecting the center axis of the hollow portion of the oxygen detection element. Also, the holding means for holding the heating member is formed separately from the metallic terminal member (i.e., the holding means is formed independently of the metallic terminal member). Thus, at least a portion of the heating member can be in contact with the inner wall surface of the hollow portion of the oxygen detection element without the metallic terminal member having special heating-member holder means. Further, assembly of the oxygen sensor does not require a jig for preliminarily attaching the heating member to the metallic terminal member, thereby reducing cost.

The term "contact" typically implies one of the following three kinds of so-called laterally-abutting structure, in which the surface of a heating portion formed at a front end portion of the heating member is laterally pressed against the inner wall surface of the hollow portion of the oxygen detection element.

(1) First it is conceivable that only a front-end portion of the surface of the heating member is in contact with the inner wall surface of the hollow portion (so-called point contact state or near point-contact state). This state of contact arises, for example, when the center axis of the heating member and that of the hollow portion intersect. In the vicinity of the heating portion of the heating member, the center axis of the heating member is laterally biased (offset) from the center axis of the hollow portion of the oxygen detection element.

(2) Next it is conceivable that the surface of the heating portion of the heating member is in contact with the inner wall surface of the hollow portion over a relatively long distance (so-called line contact state or near line-contact state). This state of contact arises, for example, when the center axis of the heating member is substantially in parallel with the center axis of the hollow portion of the oxygen detection element. The center axis of the heating member is laterally biased (offset) from the center axis of the hollow portion of the oxygen detection element.

(3) Further it is conceivable that the surface of the heating member is in contact with the inner wall surface of the hollow portion of the oxygen detection element over substantially the entire length of the heating member (so-called overall contact state or near overall-contact state). This state of contact arises, for example, when the center axis of the heating member approaches that of the hollow portion of the oxygen detection element such that the distance therebetween decreases toward the front-end side. The center axis of the heating member is laterally biased (offset) from the center axis of the hollow portion of the oxygen detection element.

Point contact, line contact, and overall contact are all applicable to the first aspect of the invention.

In the first aspect of the invention, the holding means for holding the heating member is formed separately from the metallic terminal member. Specifically, preferably, the oxygen sensor further comprises:

an external cylindrical member for accommodating the oxygen detection element;

a lead wire connected to the metallic terminal member and adapted to lead out an output from the oxygen detection element to the exterior of the oxygen sensor; and a grommet having a lead wire through-hole formed therein for passing the lead wire therethrough and fitted into a rear-end opening portion of the external cylindrical member, the grommet filling the space between the inner wall of an opening portion of the external cylindrical member and the lead wire for the sake of seal.

In this preferred oxygen sensor, the holding means is a frictional force induced between the grommet and a portion of the lead wire located within the lead wire through-hole. The grommet and the lead wire are utilized as the holding means for holding the heating member, thereby reducing cost.

To achieve the above object, an oxygen sensor according to a second aspect of the invention is characterized by comprising:

an oxygen detection element assuming the form of a hollow rod which is closed at a front end, and having electrode layers formed on inner and outer surfaces of a hollow portion thereof;

a rodlike heating member disposed within the hollow portion of the oxygen detection element and adapted to heat the oxygen detection element; and a metallic terminal member formed so as to circumferentially surround the heating member and having an attachment portion, which is fixedly attached to an inner surface of the oxygen detection element, directly or indirectly via another member.

The metallic terminal member includes at least one press portion for pressing the heating member in a direction intersecting the center axis of the hollow portion of the oxygen detection element.

The press portion causes the heating member to extend along and in contact with the inner wall surface of the hollow portion of the oxygen detection element.

According to the second aspect of the invention, the metallic terminal member does not employ special heating-member holder means, but the press portion thereof merely presses the heating member so as to cause direct contact of the heating member with and along the inner wall surface of the hollow portion of the oxygen detection element. Thus, heat generated by the heating member is efficiently transmitted to the oxygen detection element.

In the present invention, when the metallic terminal member includes at least two press portions located apart from each other in an axial direction thereof, the heating member is unlikely to come off the metallic terminal member, which would otherwise occur due to vibration, and the heating member can be stably pressed. Thus, the heating member can be maintained in stable contact with the oxygen detection element.

Preferably, the present invention is such that:

a ceramic separator having a lead wire through-hole formed therein for passing the lead wire therethrough is disposed on the rear-end portion side of the oxygen detection element;

the ceramic separator has a heating-member-end-portion accommodation hole formed therein in such a manner as to extend thereinto from a front end face thereof; and a bottom surface of the heating-member-end-portion accommodation hole is located at an axially intermediate portion of the ceramic separator and serves as positioning means for the heating member. Thus, the ceramic separator, which is an existing member, can be utilized as positioning means for the rear end portion of the heating member. Further, through insertion of the rear end portion of the heating member into the heating-member-end-portion accommodation hole, the overall length of the oxygen sensor can be reduced, thereby reducing the size of the oxygen sensor.

Preferably, at least one of the press portions is formed on the attachment portion of the present invention. Since a pressing force effected by the press portions is imposed directly on the inner circumferential surface of the attachment portion, which is fixedly attached to the inner surface of the oxygen detection element, the heating member is reliably held while being pressed in a direction intersecting the center axis of the hollow portion of the oxygen detection element. Also, the metallic terminal member is effectively prevented from having any play or coming off.

Preferably, the press portion formed on the attachment portion of the present invention is formed such that at least a portion of the circumferential wall of the attachment portion projects radially inward. A portion of the circumferential wall of the attachment portion is utilized as the press portion, whereby the press portion can reliably press the heating member in a direction intersecting the center axis of the hollow portion of the oxygen detection element. Since the press portion is an integral portion of the metallic terminal member, cost can be reduced.

The press portion of the present invention includes an integrally formed guide segment adapted to effect smooth insertion of at least a front end portion of the heating member when the heating member is to be inserted into the metallic terminal member. By virtue of the guide action of the guide segment, the heating member can be smoothly inserted into the metallic terminal member, thereby improving work efficiency. The guide segment of the press portion may extends in such a direction that the distance from the external circumferential surface of the heating element increases in a continuous or stepwise manner.

According to the present invention, a portion of the circumferential wall of the attachment portion projects toward the external circumferential surface of the heating member so as to form a protrusion portion, and the location of the protrusion portion corresponds to the location of contact between the heating member and the inner wall surface of the hollow portion of the oxygen detection element. This protrusion portion restricts the degree of freedom with respect to the radial movement (the degree of radial play) of the heating member, thereby reducing the radial play of the heating member and suppressing the axial movement of the heating member to a low level.

Preferably, the present invention is such that:

the attachment portion is inserted directly or indirectly via another member into a counter-bore portion which is formed in the oxygen detection element in such a manner as to extend axially over a predetermined length from the end face of a rear-end opening portion of the hollow portion toward a front end portion of the oxygen detection element, the counter-bore portion having a bore diameter greater than that of the hollow portion; and the position where the protrusion portion presses against the heating member is located on an extension line of the inner wall surface of the hollow portion of the oxygen detection element. Thus, the metallic terminal member does not move radially inward beyond the inner wall surface of the hollow portion. Substantially the entire outer circumferential surface of the attachment portion is in contact with the inner wall surface of the hollow portion, whereby the heating member can be easily disposed so as to extend along the inner wall surface of the hollow portion and can be prevented from having any play.

The protrusion portion of the present invention includes an integrally formed guide segment adapted to effect smooth insertion of at least a front end portion of the heating member when the heating member is to be inserted into the metallic terminal member. By virtue of the guide action of the guide segment, the heating member can be smoothly inserted into the metallic terminal member, thereby improving work efficiency. The guide segment of the protrusion portion may extend in such a direction that the distance from the external circumferential surface of the heating element increases in a continuous or stepwise manner.

BRIEF DESCRIPTION OF THE DRAWINGS

FIGS. 7(a), 7(b) and 7(c) show a left-hand side view, front view, and elevational view of a metallic internal-electrode connection member, respectively.

Figure 1:
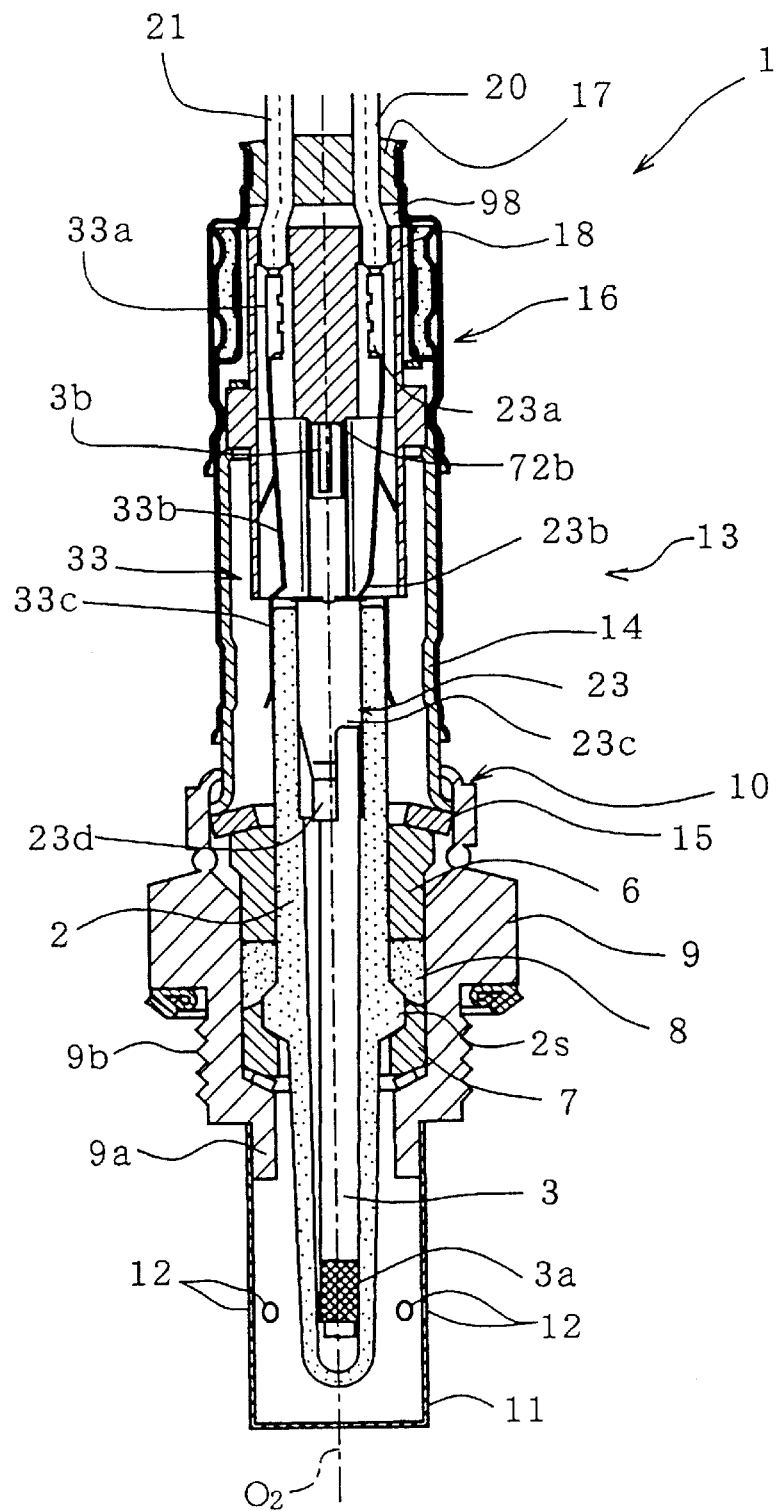
FIG. 1 is a longitudinal sectional view of an oxygen sensor of the present invention.

Reference numerals are used to identify items shown in the drawings as follows:

1: oxygen sensor
2: oxygen detection element
2a: hollow portion
2b: external electrode layer
2c: internal electrode layer
2d: counter-bore (counter-bore portion)
3: heating member
3a: heating portion
10: casing
13: external cylindrical member
17: grommet
18: ceramic separator
20, 21: lead wires
23: metallic internal-electrode connection member (metallic terminal member)
23c: engagement portion (attachment portion)
23d: lower press portion (press portion)
23d00: folding line
23d3: first guide segment (guide segment of press portion)
23e: upper press portion (press portion)
23e00: folding line
23e2: second guide segment (guide segment of press portion)
23e': cut
23e": nail-like portion
23f: protrusion portion
23f00: folding line
23f2: third guide segment (guide segment of protrusion portion)
23f: first cut
23f': nail-like portion
23h': second cut
23h": cutout portion
23i': cut for connecting start portions
23j': cut for connecting end portions
72, 91: lead wire through-holes
72a: heating-member-end-portion accommodation hole
72b: bottom surface (positioning means)
F: frictional force (holding means)
O1: center axis of heating member
O2: center axis of hollow portion of oxygen detection element

DESCRIPTION OF THE PREFERRED EMBODIMENTS

The present invention is hereinafter described in greater detail by reference to the drawings. However, the present invention should not be construed as being limited thereto.

Figure 2:
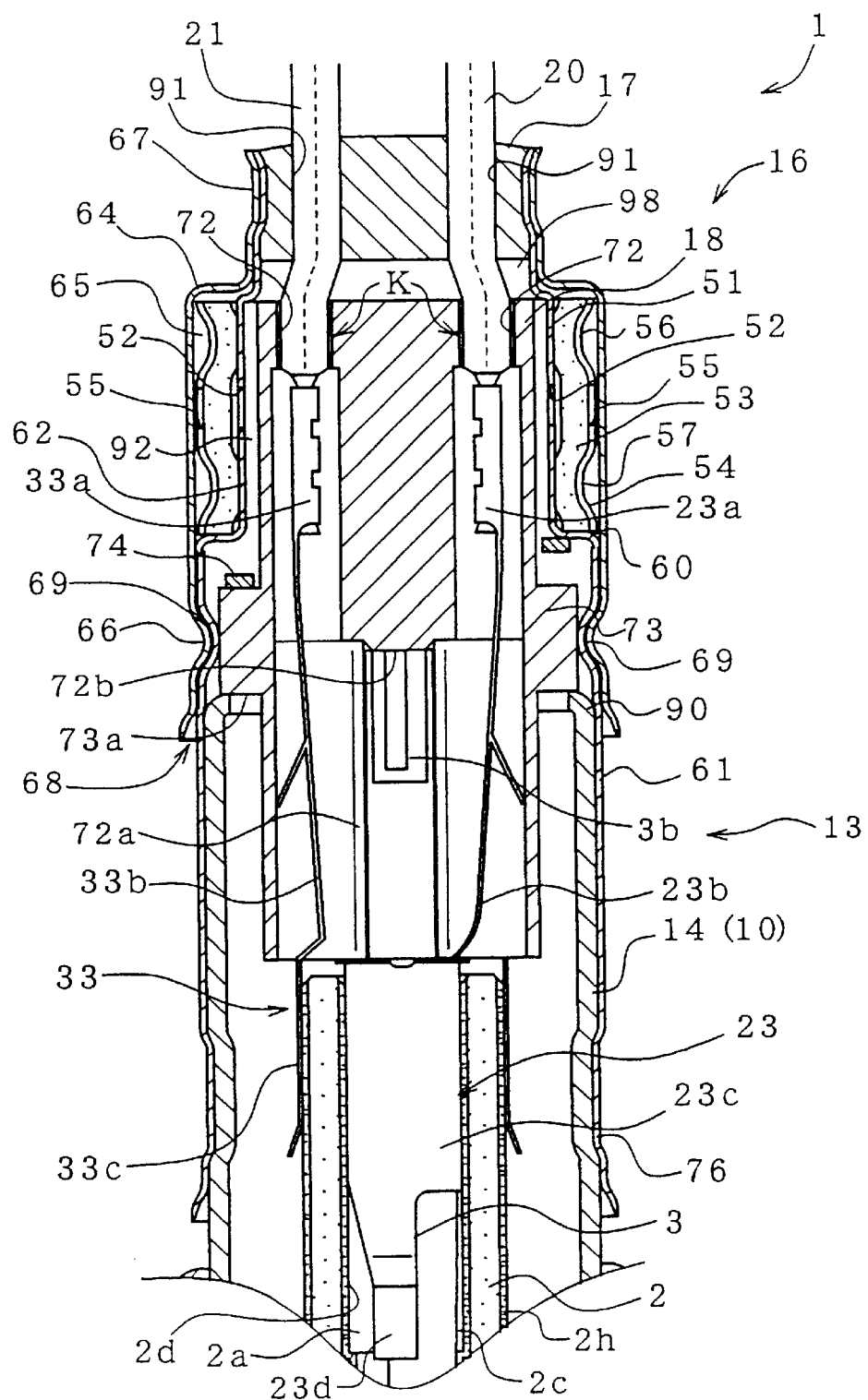
FIG. 2 is a partially enlarged longitudinal sectional view of the oxygen sensor of FIG. 1.

FIG. 1 shows the internal structure of an oxygen sensor of the present invention. FIG. 2 is an enlarged view of a main portion of the oxygen sensor. An oxygen sensor 1 includes an oxygen detection element 2, which is a solid electrolyte member assuming the form of a hollow rod which is closed at a front end, and a heating member 3 inserted into a hollow portion 2a of the oxygen detection element 2. The oxygen detection element 2 is formed into a hollow form from an oxygen-ion-conductive solid electrolyte. A typical example of such a solid electrolyte of $ZrO_2$ containing $Y_2O_3$ or CaO. Alternatively, a solid solution of $ZrO_2$ containing an oxide of an alkaline earth metal or a rare earth metal may be used. $ZrO_2$ serving as a base material may contain $HfO_2$. A metallic casing 10 is disposed to surround an intermediate portion of the oxygen detection element 2; and insulators 6 and 7 of insulating ceramic and a ceramic powder 8 of talc are disposed between the metallic casing 10 and the intermediate portion of the oxygen detection element 2. In the following description, the term "front side" or derivatives thereof refer to the side of a front end portion (closed end portion) of the oxygen detection element 2, whereas the term "rear side" or derivatives thereof refer to the side opposite the "front side."

Figure 3:
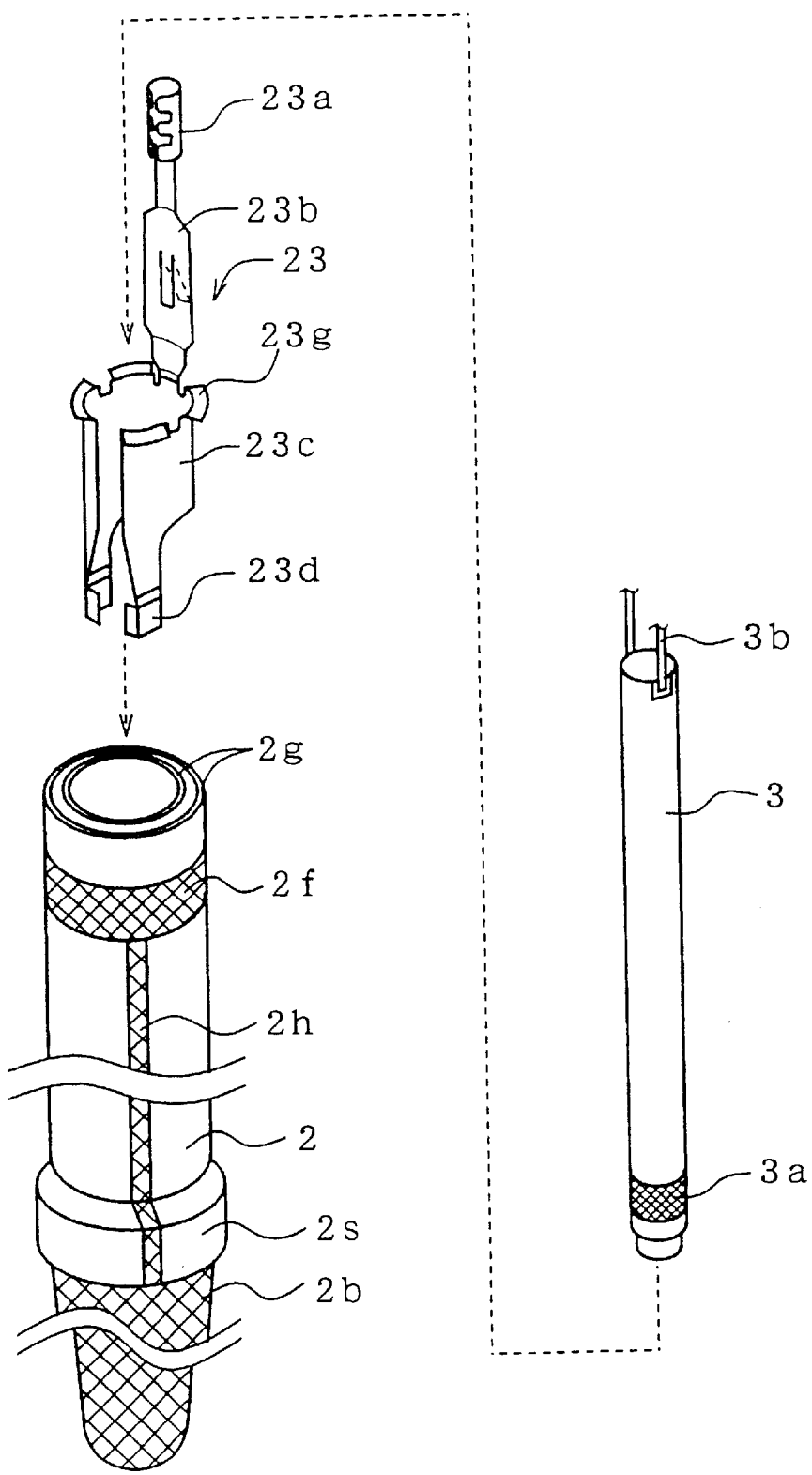
FIG. 3 is an exploded perspective view showing a stage of assembling a heating member into an oxygen detection element.

The casing 10 includes a metallic shell 9 having a threaded portion 9b. The threaded portion 9b is engaged with a mounting portion of, for example, an exhaust pipe, thereby attaching the oxygen sensor 1 to the exhaust pipe. A main cylindrical member 14 is connected to a rear-side opening portion of the metallic shell 9 in such a manner as to establish internal communication. A protector 11 is attached to a front-side opening portion of the metallic shell 9 so as to cover a front-side end portion (detection portion) of the oxygen detection element 2. A portion of the oxygen sensor 1 which is located on the front side of the threaded portion 9b is located within a system of an engine, such as within an exhaust pipe, whereas the remaining rear-side portion is located in the exterior atmosphere. As shown in FIGS. 2 and 3, an external electrode layer 2b is formed on the outer surface of the oxygen detection element 2, and an internal electrode layer 2c is formed on the inner surface of the hollow portion 2a. The external and internal electrode layers 2b and 2c are porous and formed from, for example, Pt or a Pt alloy.

The main cylindrical member 14 is caulked to the rear-side opening portion of the metallic shell 9 while a ring 15 is interposed between the main cylindrical member 14 and the insulator 6. A cylindrical filter assembly 16 is fixedly fitted onto the main cylindrical member 14. A ceramic separator 18 is disposed at the rear side of the oxygen detection element 2 substantially coaxial with the casing 10. A plurality of lead wire through-holes 72 are formed in the ceramic separator 18. Lead wires 20 and 21 for the oxygen detection element 2 and lead wires (not shown) for the heating member 3 extend through the corresponding lead wire through-holes 72. A heating-member-end-portion accommodation hole 72a is formed in the ceramic separator 18 in such a manner as to extend thereinto from the front end face thereof and such that a bottom surface 72b is located at an axially intermediate portion of the ceramic separator 18.

The filter assembly 16 assumes a cylindrical form and is substantially coaxially connected to the main cylindrical member 14 (casing 10) from the rear side. The filter assembly 16 includes a first filter holder 51 having a plurality of gas inlet holes 52 formed in a wall portion thereof. A cylindrical filter 53 (a water-repellent resin filter formed from, for example, a porous material of polytetrafluoroethylene) is disposed outside the first filter holder 51 so as to block the gas inlet holes 52. A second filter holder 54—which has one or more gas inlet holes 55 formed in a wall portion thereof—is disposed outside the filter 53 to thereby hold the filter 53 in cooperation with the first filter holder 51. A grommet 17 of rubber is elastically fitted into a rear-end opening portion of the first filter holder 51. A plurality of lead wire through-holes 91 are formed in the grommet 17 for allowing the lead wires 20, 21, etc. to extend therethrough. Thus, the grommet 17 fills the space between the external surfaces of the lead wires 20, 21, etc. and the inner surface of an opening portion of the first filter holder 51 for the purpose of seal. Notably, in the present embodiment, the filter assembly 16 is fixedly attached to the main cylindrical member 14, thereby forming an external cylindrical member 13.

However, the external cylindrical member 13 may assume a simple structure without employment of a filter assembly. In the case of the external cylindrical member 13 that does not employ a filter assembly, an airing portion may be formed on the grommet 17.

The lead wire 20 for the oxygen detection element 2 is electrically connected to the internal electrode layer 2c (FIG. 2) of the oxygen detection element 2 through a metallic internal-electrode connection member 23 (metallic terminal member). The internal electrode connector 23 includes the following integrally formed portions: a connector 23a, a lead portion 23b, an engagement portion 23c (attachment portion), and a lower press portion 23d (press portion). The other lead wire 21 is electrically connected to the external electrode layer 2b (FIG. 2) through a metallic external-electrode connection member 33. The metallic external-electrode connection member 33 includes the following integrally formed portions: a connector 33a, a lead portion 33b, and a main body portion 33c. The oxygen detection element 2 is heated by the heating member 3 disposed within the same to thereby be activated. The heating member 3 is a rodlike ceramic heater and includes a core member which contains a predominant amount of $Al_2O_3$, a heating portion 3a having a heating resistor (not shown), and two heating-member terminal portions 3b. The heating member 3 is electrically energized through lead wires (not shown) connected to the heating-member terminal portions 3b to thereby heat the oxygen detection element 2.

When the heating portion 3a of the heating member 3 is disposed locally or in a biased manner along the circumferential direction of the heating member 3, thermal energy concentrates in a smaller volume, thereby shortening heater-energizing time, or activation time. Also, when the heating portion 3a is disposed locally or in a biased manner toward a front end portion of the heating member 3, the oxygen detection element 2 can be heated quickly. Specifically, the heating portion 3a may be formed over the entirety of the heating member 3; however, this may cause dispersion of thermal energy. Thus, through biased disposition of the heating portion 3a toward a front end portion of the heating member 3, the heating member 3 generates heat locally, which is favorable. This feature of biased disposition is combined with a feature, which will be described later, that at least a front end portion of the heating member 3 is brought into contact with the inner wall surface of the hollow portion 2a of the oxygen detection element 2, thereby shortening activation time of the oxygen sensor 1.

Figure 4:
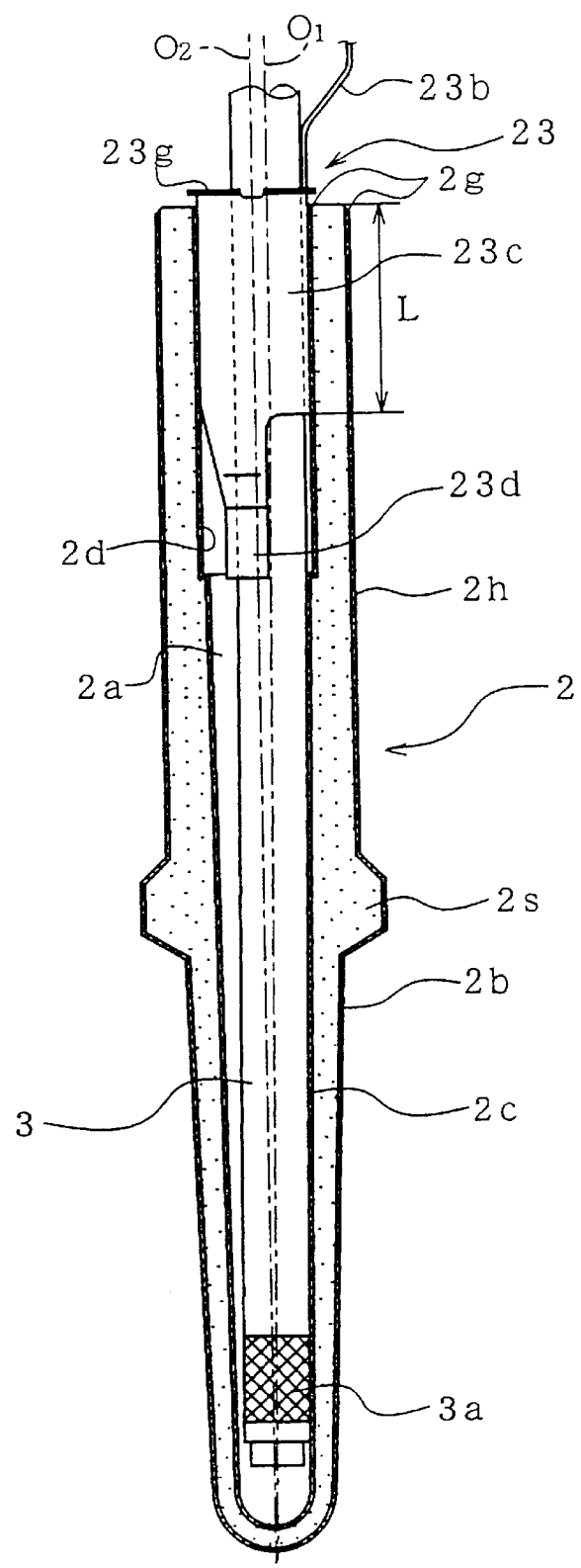
FIG. 4 is a longitudinal sectional view of the oxygen detection element shown in FIG. 3 as observed after assembly.

As shown in FIGS. 3 and 4, the heating member 3 is inserted into the metallic internal-electrode connection member 23 from the rear side. The external circumferential surface of the heating member 3 is brought into contact with the inner surface of the lower press portion 23d, which is formed at the front-end side of the metallic internal-electrode connection member 23. As a result, the lower press portion 23d presses the heating member 3 in a direction intersecting a center axis O2 of the hollow portion 2a of the oxygen detection element 2, thereby bringing at least a front-end portion of the heating member 3 into contact with the inner wall surface of the hollow portion 2a of the oxygen detection element 2. The engagement portion 23c adjacent the lower press portion 23d (press portion) is fitted into the hollow portion 2a of the oxygen detection element 2, thereby fixedly positioning the metallic internal-electrode connection member 23 with respect to the oxygen detection element 2. One end of the lead portion 23b is integrally connected to the engagement portion 23c at a circumferential position. The other end of the lead portion 23b is integrated with the connector 23a. Reference numeral 23g denotes a flange for preventing the engagement portion 23c from entering too far into the heating-member-end-portion accommodation hole 72a.

The lower press portion 23d integrated with the engagement portion 23c is composed of a pair of bent segments, each having a substantially L-shaped cross section. When the heating member 3 is inserted into the engagement portion 23c, the lower press portion 23d is elastically widened from inside. The resulting elastic restoration force; i.e., a pressing force, presses the heating member 3 in a direction intersecting the center axis O2 of the hollow portion 2a of the oxygen detection element 2.

The engagement portion 23c is formed through bending of a sheet segment into a circumferentially open-ended cylindrical form; i.e., the engagement portion 23c has a substantially C-shaped or horseshoe-like cross section taken perpendicularly to the axis.

A counter-bore 2d is formed in the hollow portion 2a of the oxygen detection element 2 in such a manner as to extend axially from the end face of a rear-end opening portion of the oxygen detection element 2 longer than an axial engagement length L of the engagement portion 23c. In order to improve release properties in compacting in the course of compacting and firing of solid electrolyte powder, the inner wall surface of the hollow portion 2a of the oxygen detection element 2 is slightly tapered such that the diameter reduces toward a bottom portion. The engagement portion 23c is directly and fixedly engaged with the wall surface of the counter-bore 2d formed in the hollow portion 2a of the oxygen detection element 2. Thus, the metallic internal-electrode connection member 23 can be fixedly situated within the oxygen detection element 2 in a smooth and reliable manner, without need to press the engagement portion 23c into the hollow portion 2a along the tapered inner wall surface, thereby preventing deformation of the engagement portion 23c and chipping of the internal electrode layer 2c.

Through formation of a chamfer 2g at an internal edge of the rear-end opening portion of the hollow portion 2a of the oxygen detection element 2, the metallic internal-electrode connection member 23 can be smoothly fitted into the oxygen detection element 2 without involvement of a defect, such as chipping, of the oxygen detection element 2. The outer circumferential surface of the engagement portion 23c is electrically connected to the inner surface of the internal electrode layer 2c through contact with the inner wall surface of the hollow portion 2a (wall surface of the counter-bore 2d) of the oxygen detection element 2. The engagement portion 23c may be brought into indirect contact with the inner wall surface of the hollow portion 2a (wall surface of the counter-bore 2d) of the oxygen detection element 2 through another member.

Referring back to FIG. 2, the metallic external-electrode connection member 33 includes the cylindrical main body portion 33c. One end of the lead portion 33b is integrally connected to the main body portion 33c at a circumferential position. The other end of the lead portion 33b is integrated with the connector 33a. A rear-end portion of the oxygen detection element 2 is inserted into the main body portion 33c in such a manner as to elastically widen the main body portion 33c from inside. As shown in FIG. 3, a conductive layer 2f assuming the shape of a circumferentially extending strip is formed on the outer surface of a rear-end portion of the oxygen detection element 2 and serves as an output terminal portion for output to the exterior of the oxygen sensor. The external electrode layer 2b is formed on the oxygen detection element 2 in such a manner as to cover the entire surface of an essential portion of the oxygen detection element 2 located on the front-end side with respect to an engagement flange portion 2s, which is formed at a substantially intermediate portion of the oxygen detection element 2. The conductive layer 2f and the external electrode layer 2b are electrically connected through a linear connection pattern layer 2h.

In the oxygen sensor 1, the atmosphere serving as a reference gas is introduced to the inner surface (internal electrode layer 2c) of the oxygen detection element 2 along the following route: a port 68 for communication with the ambient atmosphere→a groove portion 69→a gas detention space 65→a gas inlet port 55→the filter 53→a gas inlet port 52→a gap 92→a gap 98→a gap K→the hollow portion 2a. An exhaust gas is introduced through gas transmission holes 12 formed in the protector 11 and comes into contact with the outer surface (external electrode layer 2b) of the oxygen detection element 2. As a result, an electromotive force is generated in the oxygen detection element 2 by the oxygen concentration cell effect, according to the difference in oxygen concentration between the inner and outer surfaces. The thus-generated electromotive force is output in the form of a detection signal indicative of oxygen concentration in the exhaust gas. The signal is output from the internal and external electrode layers 2c and 2b (FIG. 2) through the metallic connection members 23 and 33 and lead wires 20 and 21, thereby detecting oxygen concentration in the exhaust gas.

Figure 9:
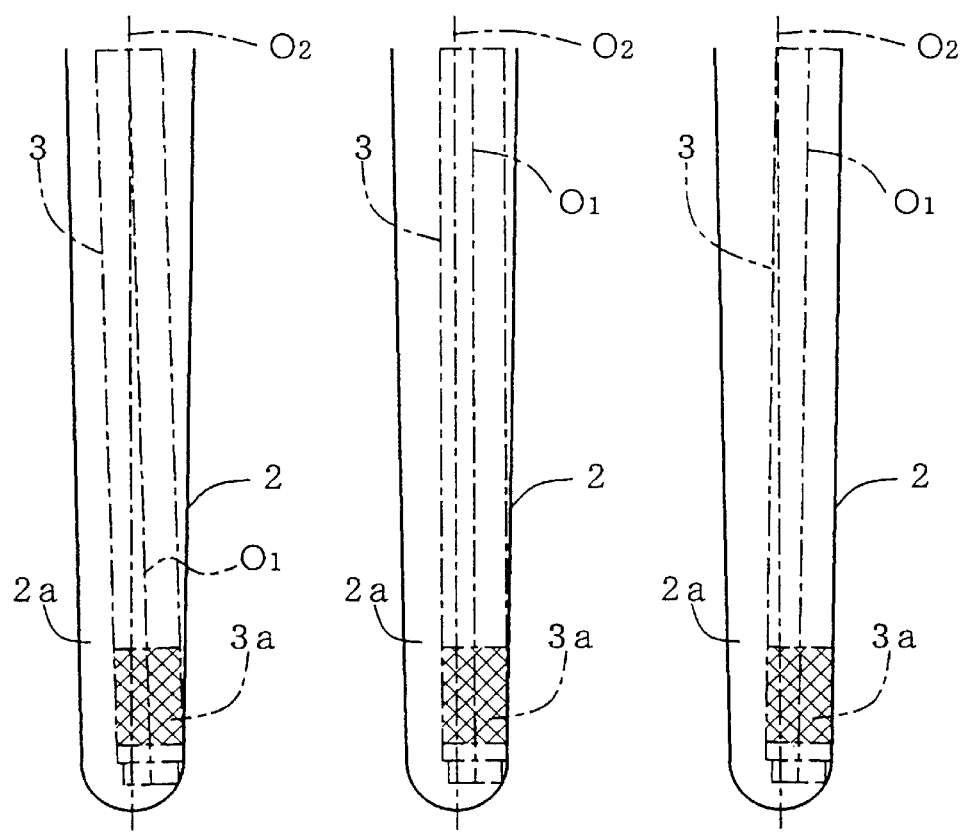
FIGS. 9(a), 9(b) and 9(c) are conceptual diagrams explaining the positional relationship between an oxygen detection element and a heating member.

Referring to FIG. 4, the lower press portion 23d presses the heating member 3 in a direction intersecting the center axis O2 of the hollow portion 2a of the oxygen detection element 2. As a result, the heating member 3 is disposed within the hollow portion 2a of the oxygen detection element 2 such that a center axis O1 of the heating member 3 is laterally biased (offset) from the center axis O2 of the hollow portion 2a. Also, at least a portion of the heating member 3 is in contact with the inner wall surface of the hollow portion 2a of the oxygen detection element 2. The positional relationship between the oxygen detection element and the heating member will be described with reference to FIG. 9.

The positional relationship between the center axis O1 of the heating member 3 and the center axis O2 of the hollow portion 2a of the oxygen detection element 2 and the positional relationship between the surface of the heating portion 3a of the heating member 3 and the inner wall surface of the hollow portion 2a of the oxygen detection element 2 are represented in the following manner.

(1) A state in which the center axis O1 of the heating member 3 and the center axis O2 of the hollow portion 2a of the oxygen detection element 2 intersect. In the vicinity of the heating portion 3a of the heating member 3, the center axis O1 of the heating member 3 is laterally biased (offset) from the center axis O2 of the hollow portion 2a of the oxygen detection element 2. Thus, there is realized the so-called lateral abutment, in which the surface of the heating portion 3a of the heating member 3 is laterally pressed against the inner wall surface of the hollow portion 2a of the oxygen detection element 2; more specifically, a so-called point contact state, in which only a front-end portion of the surface of the heating member 3a is in contact with the inner wall surface of the hollow portion 2a (See FIG. 9(a)).

(2) A state in which the center axis O1 of the heating member 3 is substantially in parallel with the center axis O2 of the hollow portion 2a of the oxygen detection element 2. The center axis O1 of the heating member 3 is laterally biased (offset) from the center axis O2 of the hollow portion 2a of the oxygen detection element 2. Thus there is realized the so-called lateral abutment, in which the surface of the heating portion 3a of the heating member 3 of the laterally pressed against the inner wall surface of the hollow portion 2a of the oxygen detection element 2; more specifically a so-called line contact state, in which the surface of the heating potion 3a of the heating member 3 is in contact with the inner wall surface of the hollow portion 2a over a relatively long distance (see FIG. 9(b)).

(2) A state in which the center axis O1 of the heating member 3 is substantially in parallel with the center axis O2 of the hollow portion 2a of the oxygen detection element 2. The center axis O1 of the heating member 3 is laterally biased (offset) from the center axis O2 of the hollow portion 2a of the oxygen detection element 2. Thus, there is realized the so-called lateral abutment, in which the surface of the heating portion 3a of the heating member 3 is laterally pressed against the inner wall surface of the hollow portion 2a of the oxygen detection element 2; more specifically a so-called line contact state, in which the surface of the heating portion 3a of the heating member 3 is in contact with the inner wall surface of the hollow portion 2a over a relatively long distance (see FIG. 9(b)).

(3) A state in which the center axis O1 of the heating member 3 approaches the center axis O2 of the hollow portion 2a of the oxygen detection element 2 such that the distance therebetween decreases toward the front side (downward in FIG. 9(c)). The center axis O1 of the heating member 3 is laterally biased (offset) from the center axis O2 of the hollow portion 2a of the oxygen detection element 2. Thus, there is realized the so-called lateral abutment, in which the surface of the heating portion 3a of the heating member 3 is laterally pressed against the inner wall surface of the hollow portion 2a of the oxygen detection element 2; more specifically, a so-called overall contact state, in which the surface of the heating member 3 is in contact with the inner wall surface of the hollow portion 2a of the oxygen detection element 2 over substantially the entire length of the heating member 3 (See FIGS. 9(c) and 4).

In the actual point contact state or line contact state, a surface contact state is established to some extent between the surface of the heating portion 3a of the heating member 3 and the inner wall surface of the hollow portion 2a of the oxygen detection element 2, depending on the pressing force which is generated by the lower press portion 23d of the metallic internal-electrode connection member 23, and other factors. However, these designations are used for convenience. In the actual entire contact state, the entire surface of the heating member 3 is not in contact with the inner wall surface of the hollow portion 2a of the oxygen detection element 2, but again this designation is used for contrast to the point contact state or the line contact state. As described previously, the inner wall surface of the hollow portion 2a of the oxygen detection element 2 is slightly tapered such that the diameter reduces toward a bottom portion. In the entire contact state shown in FIG. 9(c), the inclination angle of the center axis O1 of the heating member 3 to the center axis O2 of the hollow portion 2a of the oxygen detection element 2 substantially coincides with this taper. As seen from the above description, particularly, in the first invention, all lateral abutment features; i.e., point contact, line contact, and entire contact, are applicable.

Figure 5:
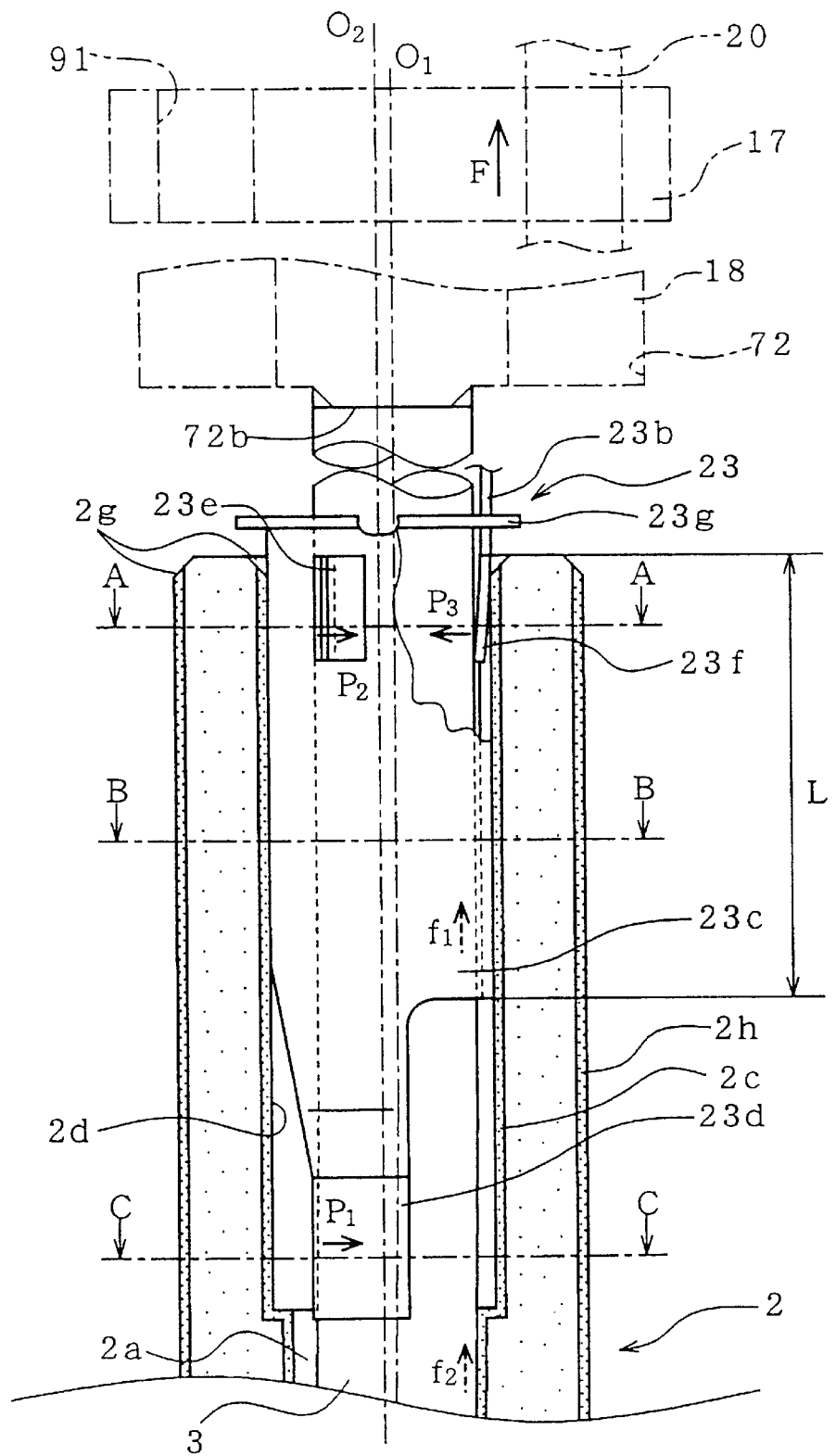
FIG. 5 is a partially enlarged longitudinal sectional view showing a main portion of FIG. 4.
Figure 6:
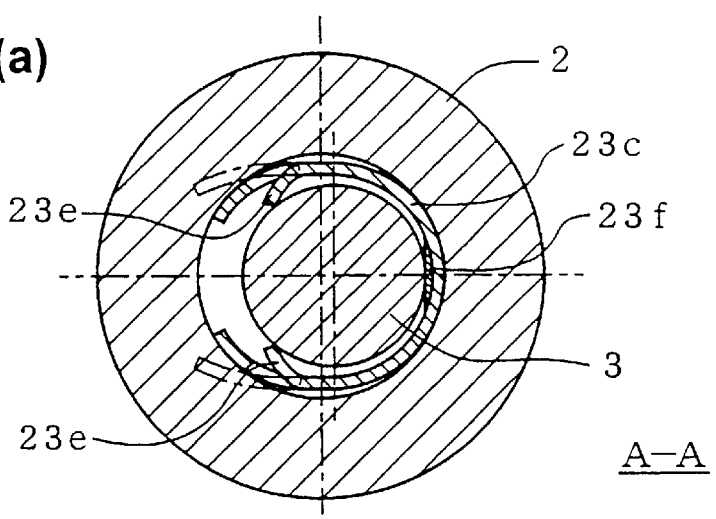
FIGS. 6(a), 6(b) and 6(c) show transverse sectional views of FIG. 5.
Figure 6:
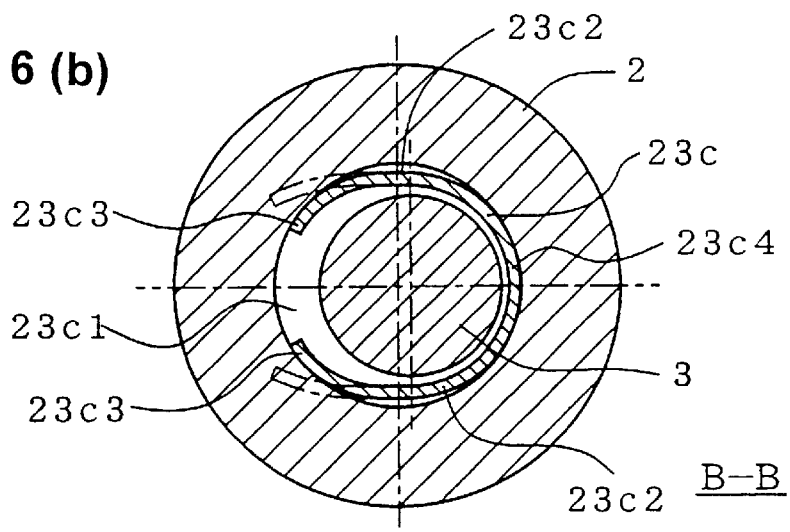
Figure 6:
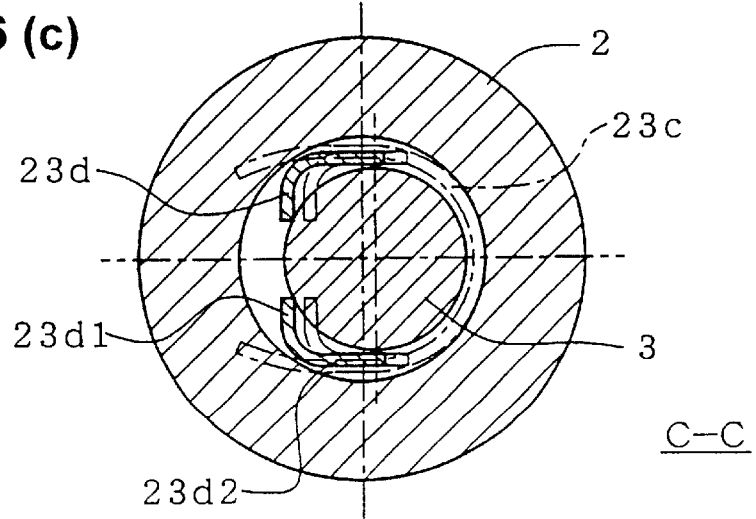

FIG. 5 is a longitudinal sectional view showing a main portion of the present invention. FIG. 6 shows transverse sectional views of FIG. 5. The metallic internal-electrode connection member 23 is inserted into the oxygen detection element 2 through the rear-end opening. The outer surface of the engagement portion 23c of the metallic internal-electrode connection member 23 is engaged with the wall surface of the counter-bore 2d, whereby the metallic internal-electrode connection member 23 is fixedly positioned within the oxygen detection element 2. The lower press portion 23d (press portion) formed at the front-end side of the metallic internal-electrode connection member 23 is composed of a pair of bent segments, each including two planes 23d1 and 23d2 (see FIG. 7) and having a substantially L-shaped cross section. When the heating member 3 is inserted into the metallic internal-electrode connection member 23 (engagement portion 23c) from the rear side, the planes 23d1 of the lower press portion 23d are elastically widened from inside. The resulting elastic restoration force; i.e., a pressing force P1, presses the heating member 3 in a direction intersecting the center axis O2 of the hollow portion 2a of the oxygen detection element 2, thereby bringing at least a portion of the heating member 3 into contact with the inner wall surface of the hollow portion 2a of the oxygen detection element 2 (see FIG. 6(c)). Notably, the planes 23d2 do not come into contact with the inserted heating member 3. Accordingly, the lower press portion 23d presses the heating member 3 in a direction intersecting the center axis O2 of the hollow portion 2a of the oxygen detection element 2. The lower press portion 23d is not intended to hold the heating member 3.

The engagement portion 23c integrated with the lower press portion 23d has an opening 23c1 such that the opening 23c1 is a portion of the circumference of the cross section of the engagement portion 23c taken perpendicularly to the axis. The engagement portion 23c includes a direction change portion 23c4, which is located opposite the opening 23c1 with respect to the axis. Thus, the engagement portion 23c has a substantially C-shaped or horseshoe-like cross section. As shown in FIG. 6(b), the engagement portion 23c includes substantially parallel linear portions 23c2, which are each circumferentially apart from the opening 23c1 by about 90° and face each other; edge portions 23c3, which are located at the opposite sides of the opening 23c1; and the direction change portion 23c4, which is located opposite the opening 23c1 with respect to the axis. As a result, the engagement portion 23c are in close contact with the inner wall surface of the hollow portion 2a of the oxygen detection element 2 at the following three portions: the edge portions 23c3 located at the opposite sides of the opening 23c1 and the arcuate portion 23c4 located opposite the opening 23c1 with respect to the axis. A gap is formed between each of the linear portions 23c2 and the inner wall surface of the hollow portion 2a (see FIG. 6(b)).

Two upper press portions 23e are provided in a portion of the circumferential wall of the engagement portion 23c which portion is disposed within the engagement length L extending axially from the end face of the rear-end opening portion of the oxygen detection element 2 toward the front-end portion of the oxygen detection element 2. The two upper press portions 23e (press portion) project radially inward and are located so as to face each other with respect to the opening 23c1. When the heating member 3 is inserted into the engagement portion 23c from the rear side, the upper press portions 23e are elastically widened from inside. The resulting elastic restoration force; i.e., a pressing force P2, presses the external surface of the heating member 3 in a direction intersecting the center axis O2 of the hollow portion 2a of the oxygen detection element 2, thereby bringing at least a portion of the heating member 3 into contact with the inner wall surface of the hollow portion 2a of the oxygen detection element 2 (see FIG. 6(a)). The upper press portions 23e; i.e., portions of the circumferential wall of the engagement portion 23c, directly press the heating member 3, thereby effectively preventing the inserted heating member 3 from having any play within the engagement portion 23c or from coming off the engagement portion 23c. Since two kinds of press portions; i.e., the upper press portions 23e and the lower press portion 23d, are located in such a manner as to be axially separated from each other, the heating member 3 can be brought in contact with and along the inner wall surface of the hollow portion 2a of the oxygen detection element 2. Since a pressing force is imposed on the heating member 3 at two positions, the heating member 3 becomes less likely to come off, which would otherwise result from vibration. Thus, the heating member 3 can be maintained in stable contact with the inner wall surface of the hollow portion 2a of the oxygen detection element 2.

Further, a portion of the circumferential wall of the engagement portion 23c projects toward the external circumferential surface of the heating member 3 so as to form a protrusion portion 23f on the same side as the side on which the heating member 3 is in contact with the inner wall surface of the hollow portion 2a of the oxygen detection element 2. This protrusion portion 23f extends across the gap between the inner circumferential surface of the metallic internal-electrode connection member 23 and the external circumferential surface of the heating member 3, thereby restricting the degree of freedom with respect to the radial movement (the degree of radial play) of the heating member 3 and thus reducing the radial play of the heating member 3 and suppressing the axial movement of the heating member 3 to a low level. This protrusion portion 23f is located opposite the two upper press portions 23e with respect to the center axis O1 of the heating member 3 and at substantially the same axial position (same height) as are the upper press portions 23e, thereby receiving the pressing force P2 of the upper press portions 23e. As shown in FIG. 5, when the protrusion portion 23f is in contact with the external circumferential surface of the heating member 3, a pressing force P3 is generated in the protrusion portion 23f in such a manner as to press the heating member 3 in an opposite direction as compared to the case of the upper press portions 23e. The heating member 3 is held between the upper press portions 23e and the protrusion portion 23f and is thus restricted in radial movement. Also, the axial movement of the heating member 3 can be suppressed to a low level.

The above-mentioned holding action effected by the upper press portions 23e and the protrusion portion 23f is particularly effective, for example, when, as a result of a springing stone hitting the external cylindrical member 13 and causing deformation of the external cylindrical member 13 or as a result of the ceramic separator 18 slightly shifting in a radial direction in the course of attachment thereof, a force is exerted on the heating member 3 in opposition to the pressing forces P1 and P2 derived from the lower and upper press portions 23d and 23e, respectively. However, in some cases, the protrusion member 23f may extend across the above-mentioned gap without generation of the pressing force P3 or with mere generation of a considerably small pressing force P3. Notably, the position where the protrusion portion 23f presses against the heating member 3 is located on an extension line of the inner wall surface of the hollow portion 2a of the oxygen detection element 2. Thus, the metallic internal-electrode connection member 23 does not move radially inward beyond the inner wall surface of the hollow portion 2a, whereby the heating member 3 can be easily disposed so as to extend along the inner wall surface of the hollow portion 2a.

The metallic internal-electrode connection member 23 is connected to the lead wire 20 by means of the engagement portion 23c, the lead portion 23b, and the connector 23a. The lead wire 20 is held in the lead wire through-hole 91 formed in the grommet 17, whereby the space between the external surface of the lead wire 20 and the inner surface of an opening portion of the first filter holder 51 is filled with the grommet 17 for the sake of seal. When the oxygen sensor 1 is positioned with the rear side thereof facing up, a frictional force (thrust force) F is generated on the contact surfaces of the lead wire 20 and the grommet 17 in such a manner as to act against gravity exerted on the metallic internal-electrode connection member 23 and the heating member 3. The frictional force F serves as holding means for holding (fixedly positioning) the heating member 3. Notably, frictional forces f1 and f2 are generated as a result of contact between the heating member 3 and the engagement portion 23c and between the heating member 3 and the inner wall surface of the hollow portion 2a of the oxygen detection element 2, respectively; however, these frictional forces f1 and f2 are conceivably small as compared with the frictional force F.

As mentioned previously, the heating-member-end-portion accommodation hole 72a is formed in the ceramic separator 18. The diameter of the accommodation hole 72a is rendered greater than the external diameter of the heating member 3, thereby allowing the rear end portion of the heating member 3 to be inclined within a predetermined range in association with biased disposition of the heating member 3 with respect to the hollow portion 2a of the oxygen detection element 2.

FIG. 7 shows the details of the metallic internal-electrode connection member 23. A blank shown in the development of FIG. 7(c) is blanked out from a conductive sheet and is formed into the metallic internal-electrode connection member 23, which includes the following integral portions: the connector 23a, the lead portion 23b, the engagement portion 23c, and the lower press portion 23d. The engagement portion 23c is formed through bending so as to assume a cylindrical form that has the opening 23c 1 formed at a circumferential portion thereof. Thus, the engagement portion 23c has a substantially C-shaped or horseshoe-like cross section taken perpendicularly to the axis. The lower press portion 23d is formed through bending so as to assume a substantially L-shaped cross section. The connector 23a is formed through bending so as to include an upright portion.

In the course of blanking, a cute 23f' is formed along the centerline in a central region of the engagement portion 23c in such a manner as to be open at the upper side and have a direction change portion at the lower side (a shape of a squarish letter U in FIG. 7(c)). Also, in the course of blanking, two cuts 23e' are formed on opposite sides of the cut 23f' in such a manner as to face each other with respect to the centerline. Each of the cuts 23e' is open at the near side as viewed from the centerline and has a direction change portion at the far side (a shape of a lying squarish letter U in FIG. 7(c)).

The method for forming the cut 23f' and the protrusion portion 23f will next be described in detail. First, the cut 23f' is formed so as to include the following portions: a start portion 23f1', which is located at the base-end-side relative to insertion of the heating member 3 into the metallic internal-electrode connection member 23; a direction change portion 23f2', which is located at the front-end side relative to the insertion; and an end portion 23f3', which is located at the base-end-side relative to the insertion. After the metallic internal-electrode connection member 23 is formed through bending, a portion located under a folding reference line 23f0' (a portion located at the front-end side relative to insertion of the heating member) is folded in a radially inward direction of the engagement portion 23c along the folding reference line 23f0', which is located at the side of an upper opening defined by the cut 23f' (at the base-end-side relative to insertion of the heating member). That is, a nail-like portion 23f" defined by the cut 23f$\alpha$ is folded to thereby form the protrusion portion 23f.

The method for forming the cut 23e' and the upper press portion 23e will next be described in detail. First, the cut 23e' is formed so as to include the following portions: a start portion 23e1', which is located at the base-end-side relative to insertion of the heating member 3 into the metallic internal-electrode connection member 23; a direction change portion 23e2', which is located at the intermediate region between the base-end-side and the front-end side relative to the insertion; and an end portion 23e3', which is located at the front-end side relative to the insertion. After the metallic internal-electrode connection member 23 is formed through bending, a nail-like portion 23e" defined by the cut 23e' is folded in a radially inward direction of the engagement portion 23c along a folding reference line 23e0', which is located at the side of an opening defined by the cut 23e' (at the centerline side). Thus are formed two upper press portions 23e.

The cuts 23f' and 23e used for forming the protrusion portion 23f and the upper press portion 23e may assume any form, such as a shape of a letter U. Also, the number of cuts 23f' and 23e may be decreased or increased. In order to form the portions 23f and 23e, swelled portions may be integrally formed through press-working, or separately formed protrusion portions may be attached.

Figure 8:
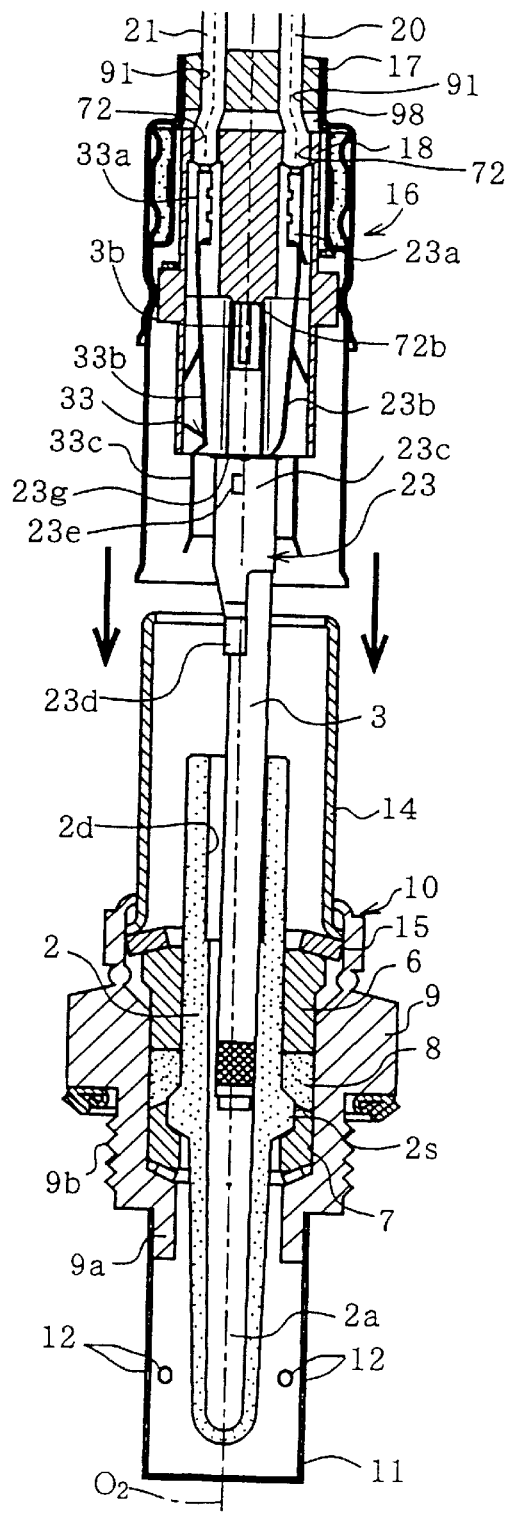
FIGS. 8(a) and 8(b) are views showing an example of a procedure for assembling the oxygen sensor of FIG. 1.
Figure 8:
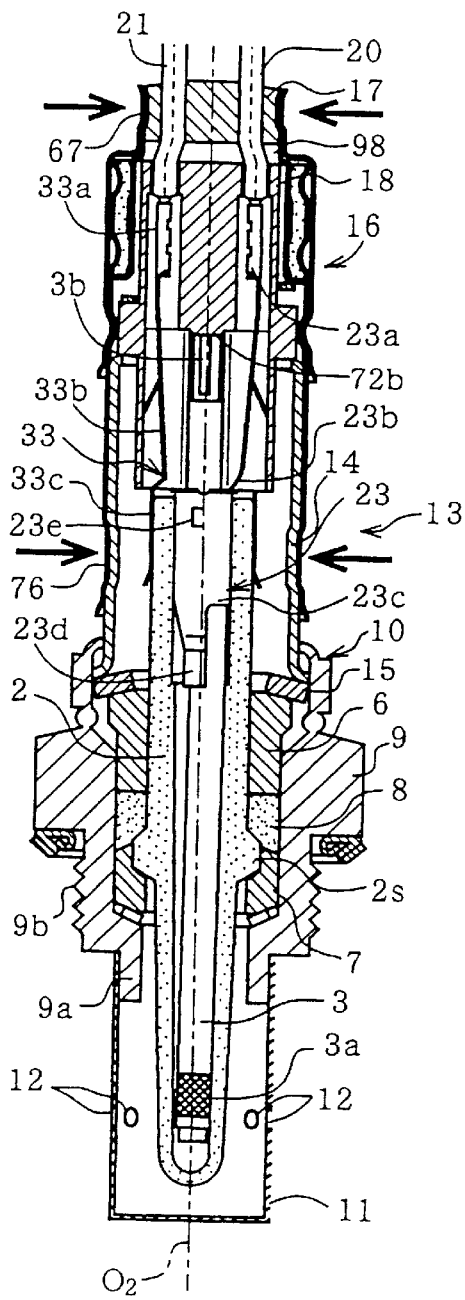

FIG. 8 shows an example of an assembling procedure for an oxygen sensor. First, the heating member 3 is inserted into the metallic internal-electrode connection member 23 from the rear side. The heating member 3 is held in radial directions by means of the following portions of the metallic internal-electrode connection member 23: the lower press portion 23d, the upper press portions 23e, and the protrusion portion 23f. In this state, the lead wire 20 connected to the metallic internal-electrode connection member 23 is led to the outside through the lead wire through-hole 72 formed in the ceramic separator 18 and then through the lead wire through-hole 91 formed in the grommet 17. The metallic internal-electrode connection member 23 is disposed such that the flange 23g abuts the front-end face of the ceramic separator 18. The rear-end portion of the heating member 3 rests on the bottom surface 72b of the heating-member-end-portion accommodation hole 72a, whereby the heating member 3 is axially positioned. The lead wire 21 connected to the metallic external-electrode connection member 33 is sequentially led to the outside through the lead wire through-holes 72 and 91. In a separate step, the oxygen detection element 2 is installed in the casing 10. The rear-end side of the casing 10, in which the oxygen detection element 2 is installed, and the front-end side of the filter assembly 16, in which the metallic electrode connection members 23 and 33 and the heating member 3 are installed, are caused to relatively approach each other. As a result, the heating member 3 is gradually inserted into the hollow portion 2a of the oxygen detection element 2, while the inner wall surface of the hollow portion 2a serves as a guide (FIG. 8(a)). Herein, the expression "relatively approach" denotes that either the casing 10 or the filter assembly 16 is moved while the other is held stationary or that both the casing filter 10 and the filter assembly 16 are moved in opposite directions, thereby causing both to approach each other.

Then, the engagement portion 23c of the metallic internal-electrode connection member 23 is inserted into the hollow portion 2a of the oxygen detection element 2 through the rear-end opening portion of the hollow portion 2a such that the external surface of the engagement portion 23c is fitted to the wall surface of the counter-bore 2d. At substantially the same time, the outer circumferential surface of the oxygen detection element 2 is inserted into the metallic exterior-electrode connection member 33. At this time, the upper press portions 23e and the lower press portion 23d press the heating member 3 in a direction intersecting the center axis O2 of the hollow portion 2a of the oxygen detection element 2, whereby the heating member 3 is brought into contact with the inner wall surface of the hollow portion 2a of the oxygen detection element 2 in the entire contact state. When a predetermined insertion position is reached, the grommet 17 and the first filter holder 51 are caulked together to thereby form a grommet-caulked portion 67. The frictional force F generated on the contact surfaces of the grommet 17 and the lead wire 20 serves as holding means for holding the heating member 3. Finally, a casing-caulked portion 76 is formed (FIG. 8(b)).

It is to be noted that the following assembly method may be employed. When the casing 10 and the filter assembly 16 are assembled together in the step shown in FIG. 8(a), the front-end portion of the ceramic separator 18, into which the metallic electrode connection members 23 and 33 and the heating member 3 have been installed in advance, is inserted into the main cylindrical member 14 through the rear-end opening portion of the same. In this case, the heating member 3 is gradually inserted into the hollow portion 2a of the oxygen detection element 2, while the inner wall surface of the hollow portion 2a serves as a guide. The engagement portion 23c of the metallic internal-electrode connection member 23 is inserted into the hollow portion 2a of the oxygen detection element 2 such that the external surface of the engagement portion 23c is fitted to the wall surface of the counter-bore 2d. At substantially the same time, the outer circumferential surface of the oxygen detection element 2 is inserted into the metallic exterior-electrode connection member 33. At this time, the upper press portions 23e and the lower press portion 23d press the external surface of the heating member 3 in a direction intersecting the center axis O2 of the hollow portion 2a of the oxygen detection element 2, whereby the heating member 3 is brought into contact with the inner wall surface of the hollow portion 2a of the oxygen detection element 2 in the entire contact state. Subsequently, while the lead wires 20 and 21 are being led to the outside through the lead wire through-holes 91 formed in the grommet 17, the front-end portion of the filter assembly 16 and the rear-end portion of the casing 10 are caused to relatively approach each other to thereby fit the filter assembly 16 onto the casing 10.

Figure 10:
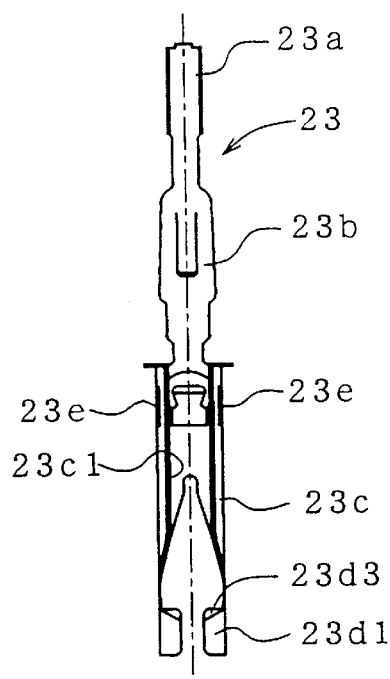
FIGS. 10(a), 10(b) and 10(c) are a left-hand side view, front view, and elevational view showing a modified embodiment of the metallic internal-electrode connection member of FIG. 7.
Figure 10:
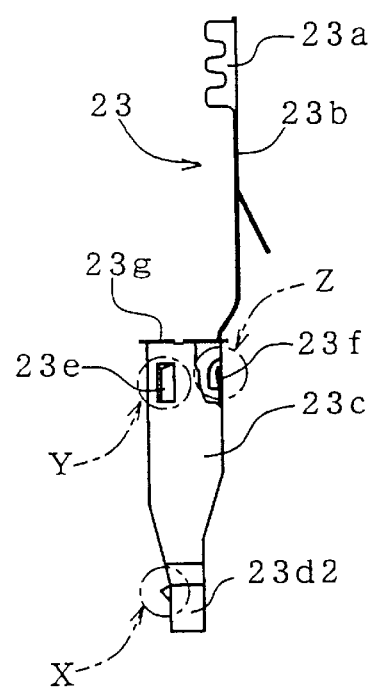
Figure 10:
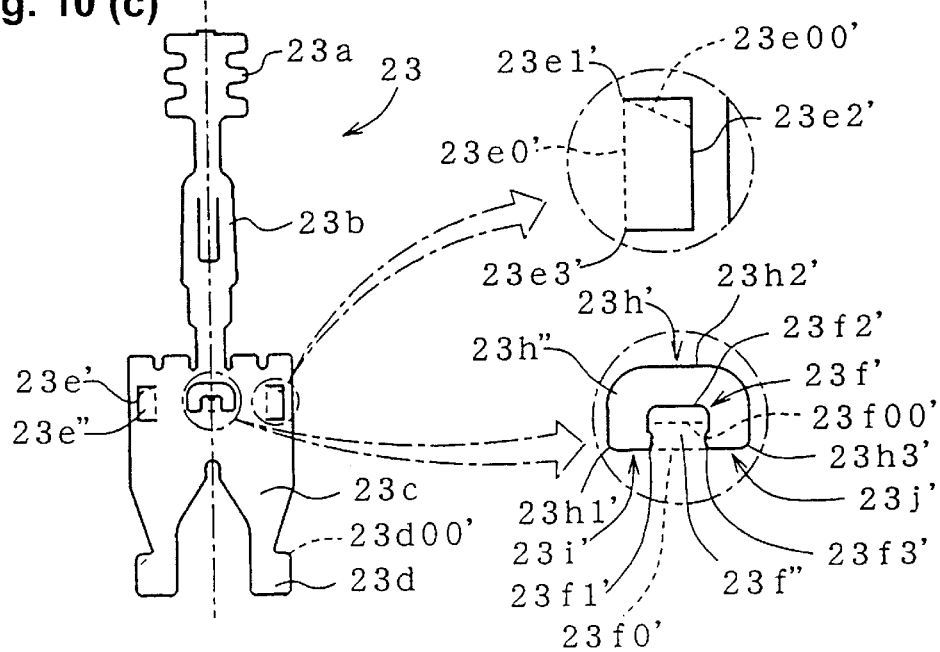
Figure 11:
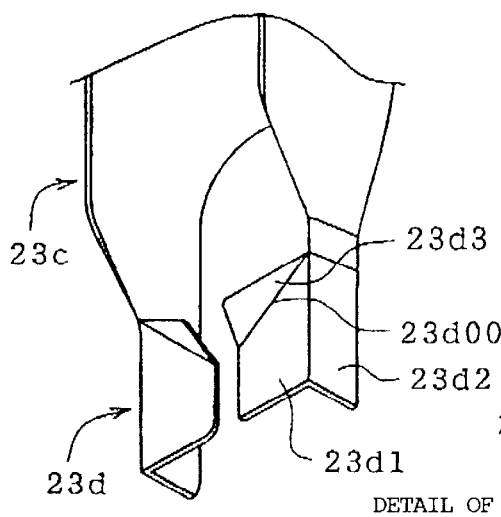
FIGS. 11(a), 11(b), 11(c) and 11(d) are detailed views of X portion, Y portion and Z portion in FIG. 10(b).
Figure 11:
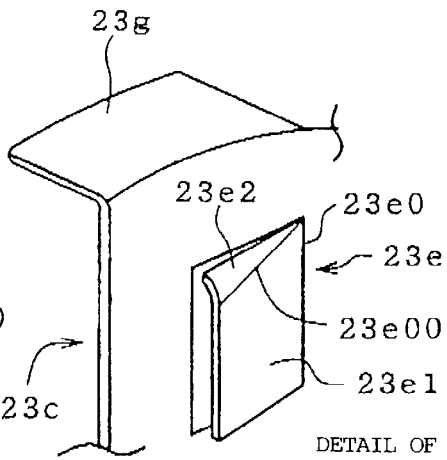
Figure 11:
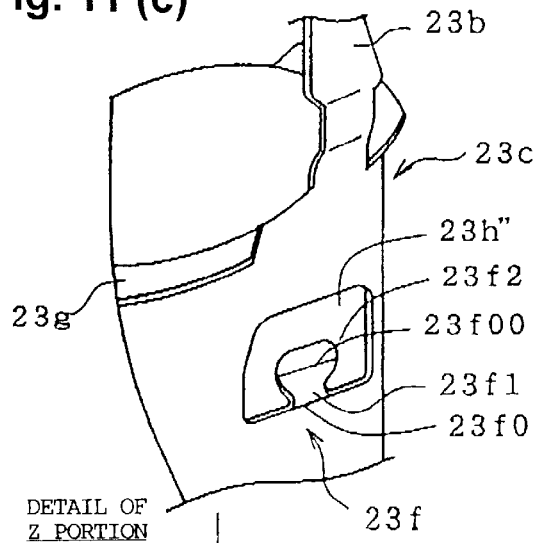
Figure 11:
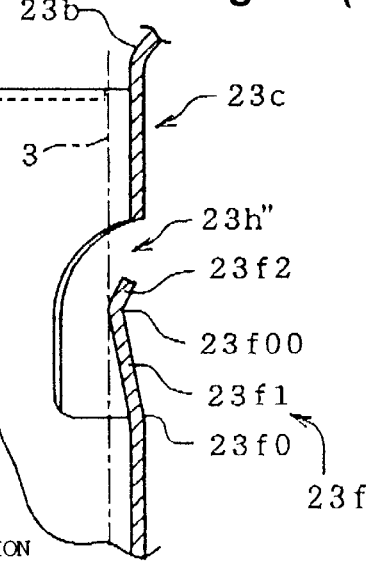

Next will be described another embodiment of the oxygen sensor, which employs a metallic internal-electrode connection member different from that of FIG. 7. Another embodiment of the metallic internal-electrode connection member shown in FIGS. 10 and 11 includes the following modifications (1)–(4) as compared with the metallic internal-electrode connection member of FIG. 7. Features common to FIGS. 7, 10, and 11 are denoted by common reference numerals, and description thereof is omitted.

(1) A first guide segment 23d3 (a guide segment of a press portion) is integrally formed at a rear-end portion of the plane 23d1, which constitutes the lower press portion 23d (press portion), for guiding at least a front-end portion relative to insertion of the heating member 3 along the axial direction of the metallic internal-electrode connection member 23. Specifically, an oblique folding line 23d00 (folding reference line 23d00') is formed at the rear-end portion of the plane 23d1. A portion located at the rear side with respect to the folding line 23d00 is bent radially outward. Thus, the first guide segment 23d3 is integrally formed at the rear-end portion of the plane 23d1 in such a manner as to expand away from the external circumferential surface of the heating member 3 (radially outward) at the base-end-side relative to insertion of the heating member 3 into the metallic internal-electrode connection member 23 (see FIG. 11 (a)). Since the first guide segment 23d3—which is located at the base-end-side relative to insertion of the heating member 3—expands away from the external circumferential surface of the heating member 3, the first guide segment 23d3 effects a guide action for smooth insertion of the heating member 3.

(2) A second guide segment 23e2 (a guide segment of a press portion) is integrally formed at a rear-end portion of a main portion 23e1, which constitutes the upper press portion 23e (press portion), for guiding at least a front-end portion relative to insertion of the heating member 3 along the axial direction of the metallic internal-electrode connection member 23. Specifically, an oblique folding line 23e00 (folding reference line 23e00') is formed at the rear-end portion of the main portion 23e1 (nail-like portion 23e"). A portion located at the rear-end side with respect to the folding line 23e00 is bent radially outward. Thus, at the base-end-side relative to insertion of the heating member 3 into the metallic internal-electrode connection member 23, the second guide segment 23e2 is integrally formed at the rear-end portion of the main portion 23e1 to bend toward a direction (radially outward direction) such that the second guide segment 23e2 gradually separates from the external circumferential surface of the heating member 3 (see FIG. 11 (b)). Since the second guide segment 23e2—which is located at the base-end-side relative to insertion of the heating member 3—bends toward a direction (radially outward direction) such that the second guide segment 23e2 gradually separates from the external circumferential surface of the heating member 3, the second guide segment 23e2 effects a guide action for smooth insertion of the heating member 3.

(3) First, a first cut 23f' is formed in the engagement portion 23c. Specifically, the first cut 23f' of a mushroom or tongue shape is formed so as to include the following portions: a first start portion 23f1', which is located at the front-end side relative to insertion of the heating member 3 into the metallic internal-electrode connection member 23; a first direction change portion 23f2', which is located at the base-end-side relative to the insertion; and a first end portion 23f3', which is located at the front-end side relative to the insertion (FIG. 10(c)). A nail-like portion 23f' enclosed by the first cut 23f' is bent radially inward along a folding line 23f0 (folding reference line 23f0') to thereby form a protrusion portion 23f Thus, the protrusion portion 23f is bent toward the external circumferential surface of the heating member 3 (see FIG. 11(c)).

Next, in the engagement portion 23c, a second cut 23h' is formed outside the first cut 23'. Specifically, the second cut 23h' of a semicylindrical or dome shape is formed so as to include the following portions: a second start portion 23h1', which is located outside the first cut 23f' and at the front-end side relative to insertion of the heating member 3 into the metallic internal-electrode connection member 23; a second direction change portion 23h2', which has a diameter greater than that of the first direction change portion 23f2' and is located at the base-end-side relative to the insertion; and a second end portion 23h3', which is located outside the first cut 23f' and at the front-end side relative to the insertion (FIG. 10(c)).

The first start portion 23f1' and the second start portion 23h1' are connected by means of a cut 23i' for connecting the start portions. The first end portion 23f3' and the second end portion 23h3' are connected by means of a cut 23j' for connecting the end portions. As a result, a region enclosed by the first cut 23f', the second cut 23h', the cut 23i' for connecting the start portions, and the cut 23j' for connecting the end portions is cut out, thereby forming a cutout portion 23h" (see FIG. 10(c)).

The protrusion portion 23f may bend elastically about a line (folding line 23f 0 in FIG. 11(c)) connecting the first start portion 23f1' and the first end portion 23f3'—which are located at the front-end side relative to insertion of the heating member 3 into the metallic internal-electrode connection member 23. Therefore, the protrusion portion 23f effects a cushioning action so as to ease an impact force received from the heating member 3 for prevention of damage to the heating member 3. The cutout portion 23h" improves a cushioning effect (a radially movable range is increased) which the protrusion portion 23f yields with respect to the pressing forces P1 and P2. Thus, even when the pressing forces P1 and P2 are increased or when the heating member 3 vibrates, damage to the heating member 3 is unlikely to occur. Notably, the first cut 23' and the second cut 23h' may assume any form other than the illustrated forms as appropriate.

(4) A third guide segment 23f2 (a guide segment of a protrusion portion) is integrally formed at a rear-end portion of a main portion 23f1, which constitutes the protrusion portion 23f, for guiding at least a front-end portion relative to insertion of the heating member 3 along the axial direction of the metallic internal-electrode connection member 23. Specifically, a folding line 23f00 (folding reference line 23f00') is formed widthwise at the rear-end portion (front-end portion) of the main portion 23f1 (nail-like portion 23f"). A portion located at the rear side with respect to the folding line 23f00 is bent radially outward. Thus, the third guide segment 23f2 is integrally formed at the rear-end portion of the main portion 23f1 in such a manner as to expand away from the external circumferential surface of the heating member 3 (radially outward) at the base-end-side relative to insertion of the heating member 3 into the metallic internal-electrode connection member 23. Thus, the protrusion portion 23f assumes the form of a character < or the form of a letter V as viewed from the front thereof by means of the main portion 23f1, which is bent radially inward, and the guide segment 23f2, which is bent radially outward (see FIG. 11(c)). Merely by bending radially outward the portion located at the rear side with respect to the folding line 23f00, the third guide segment 23f2, which expands away from the external circumferential surface of the heating member 3, can be easily obtained. Thus, insertion of the heating member 3 becomes smooth, thereby improving work efficiency.

Figure 12:
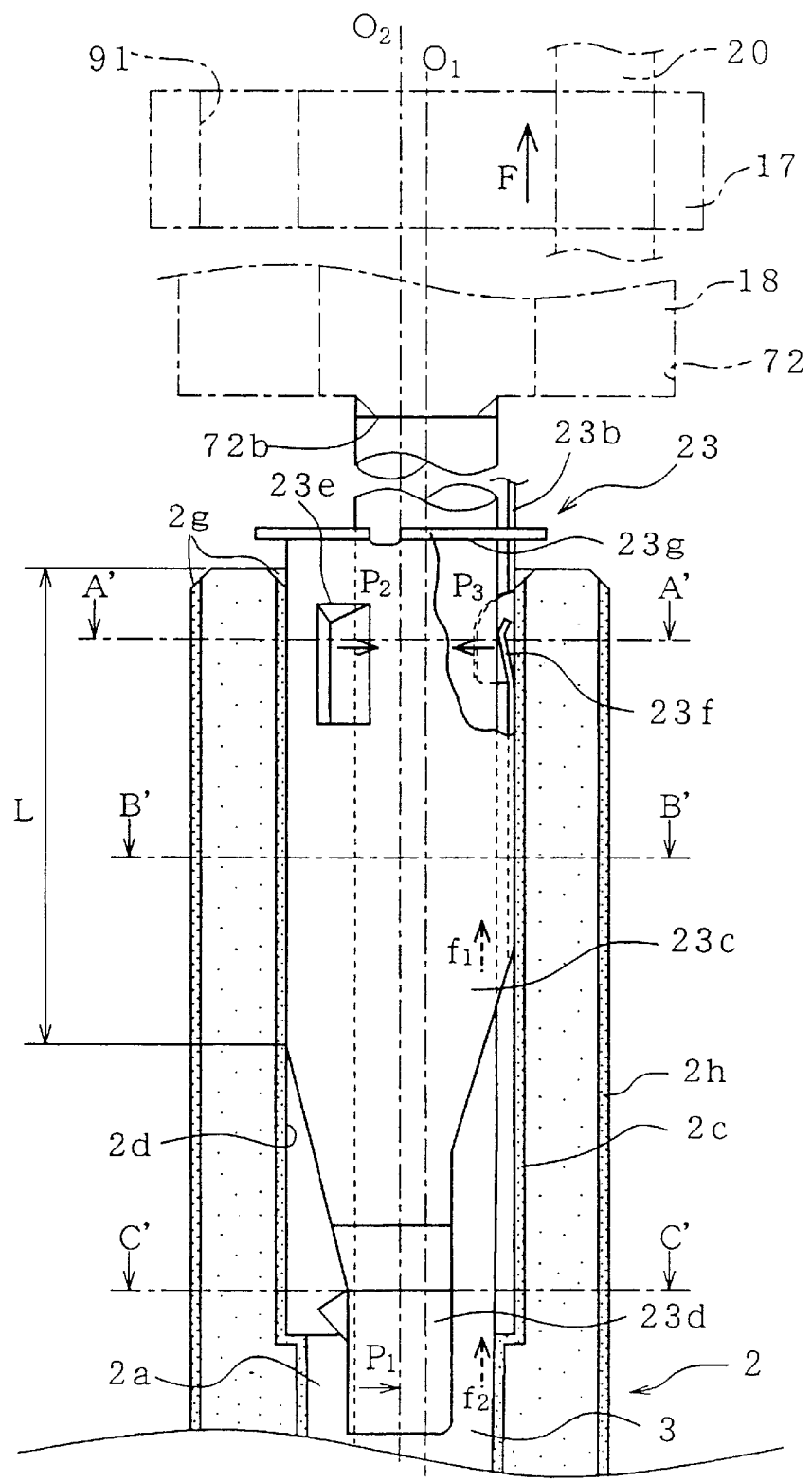
FIG. 12 is a longitudinal sectional view showing installation of the metallic internal-electrode connection member of FIG. 10 in an oxygen detection element.
Figure 13:
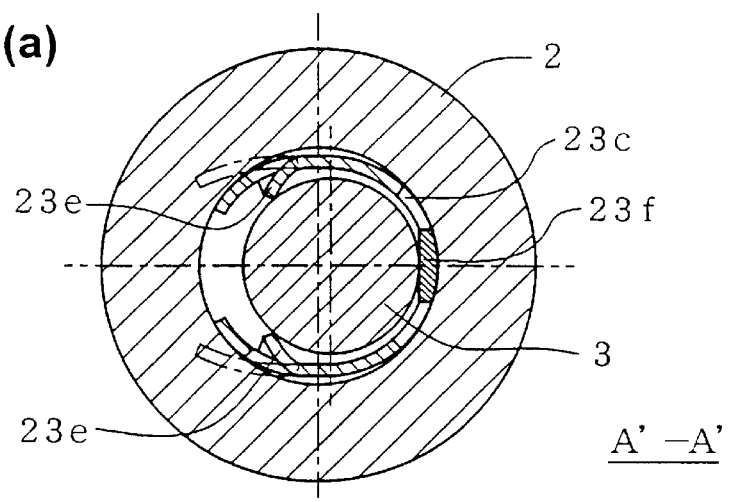
FIGS. 13(a), 13(b) and 13(c) are transverse sectional views of FIG. 12.
Figure 13:
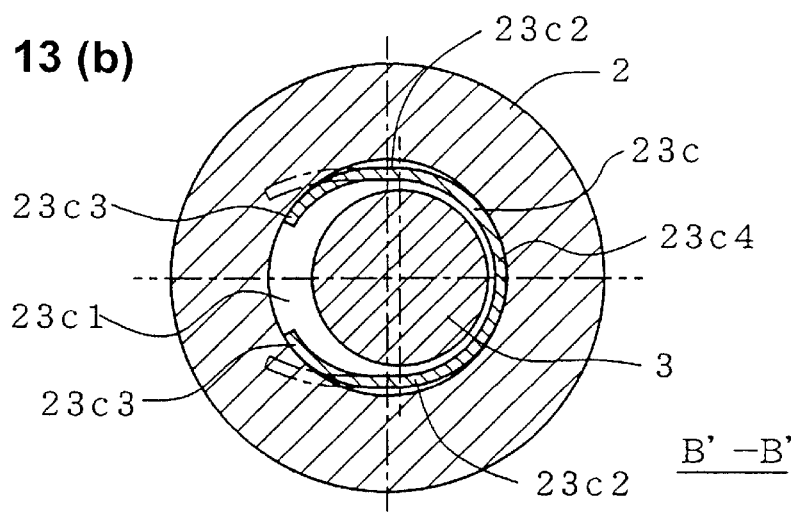
Figure 13:
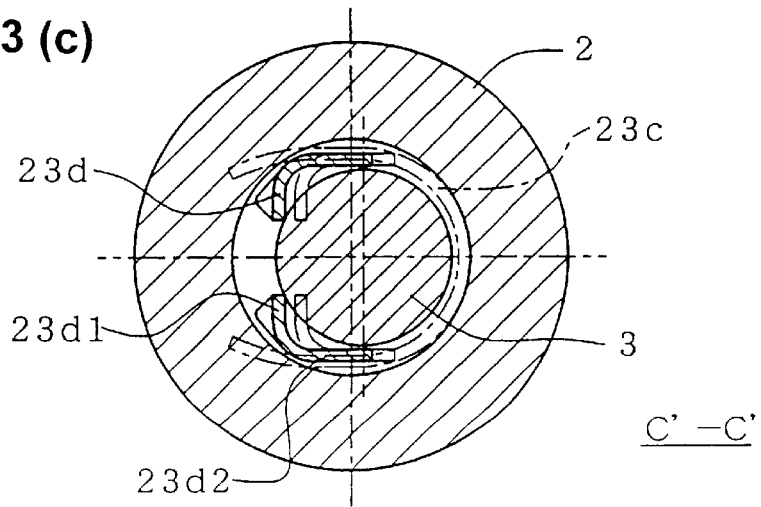

FIGS. 12 and 13 show the state of installation of the metallic internal-electrode connection member of FIG. 10 and correspond to FIGS. 5 and 6, respectively, showing the first embodiment.

Figure 14:
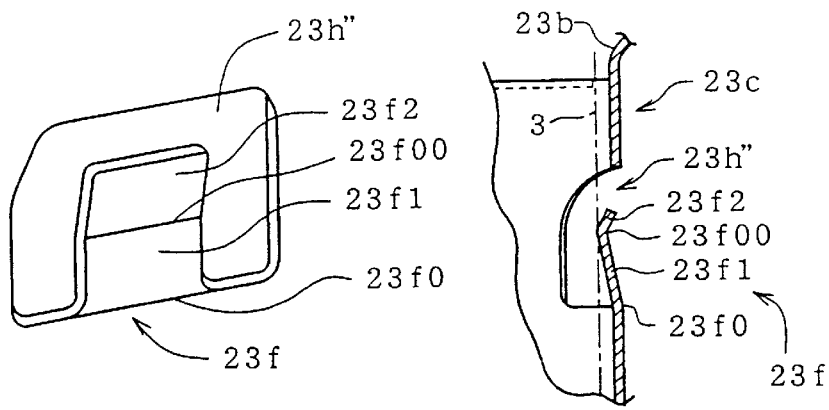
FIGS. 14(a), 14(b) and 14(c) are perspective views and sectional views showing other embodiments which replace the protrusion portions of FIGS. 11(c) and 11(d).
Figure 14:
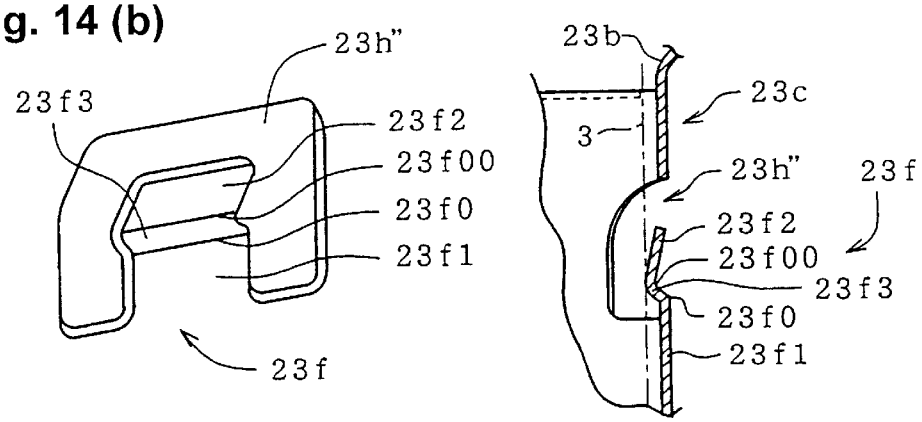
Figure 14:
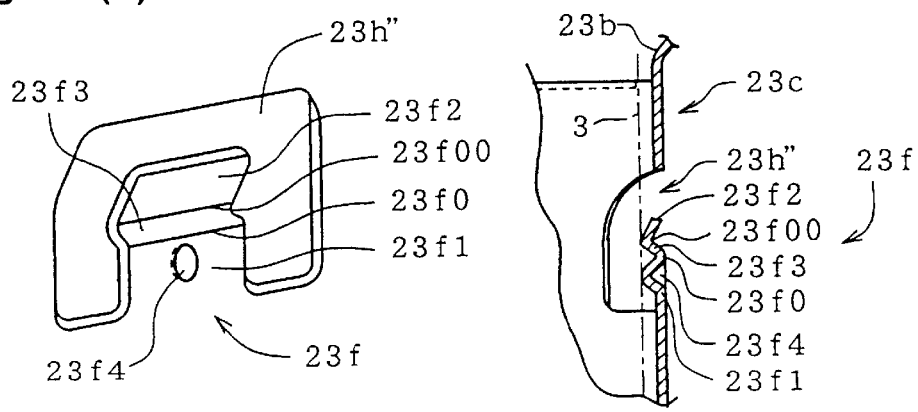

FIG. 14 shows other embodiments which replace the protrusion portion shown in FIGS. 11(c) and 11(d).

FIG. 14(a) shows a protrusion portion 23f having a substantially rectangular form. FIG. 14(b) shows a protrusion portion 23f which has a substantially rectangular form and in which a groove-like bend portion 23f3 is formed between a main portion 23f1 and a third guide segment 23f2. The groove-like bend portion 23f3 is bent radially inward and assumes a substantially arcuate form as viewed from the front side thereof. As a result of employment of the bend portion 23f3, a folding line 23f0 is shifted from the position of the line connecting the first start portion 23f1' and the first end portion 23f3' of the first cut 23f (see FIG. 10(c)) to an axially intermediate position on the protrusion portion 23f. An embodiment of FIG. 14(c) is obtained through further modification of that of FIG. 14(b). A main portion 23f1 includes a hemispheric swelled portion 23f4 which projects radially inward. Accordingly, as in the case of FIG. 14(b), a folding line 23f0 is shifted to an axially intermediate position on the protrusion portion 23f. As shown in the sectional view of FIG. 14(c), the heating member 3 may be supported by two inner surface portions of the swelled portion 23f4 and the bend portion 23f3.

Figure 15:
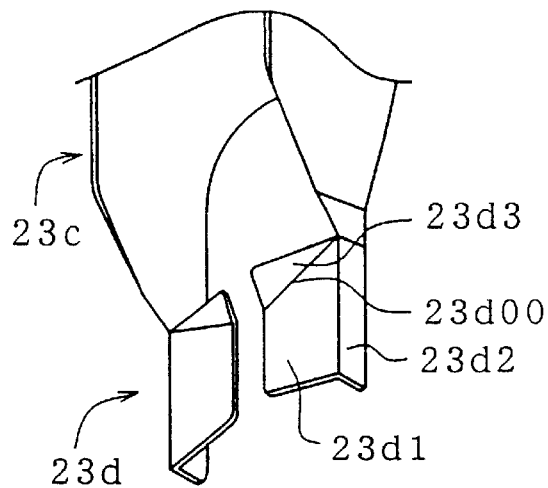
FIGS. 15(a), 15(b) and 15(c) are perspective views showing other embodiments which replace the lower press portion of FIG. 11(a).
Figure 15:
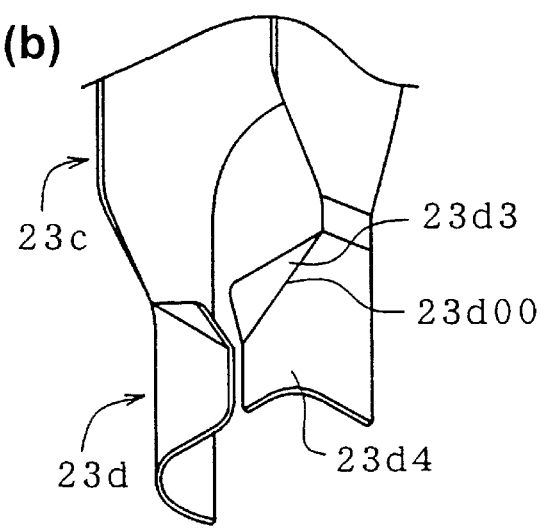
Figure 15:
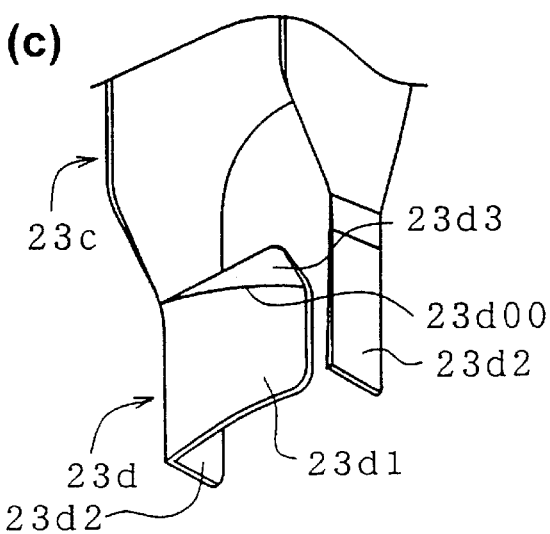

FIG. 15 shows other embodiments which replaces the lower press portion of FIG. 11(a).

FIG. 15(a) shows a lower press portion 23d in which a plane 23d1 is inclined such that two intersecting planes 23d1 and 23d2 form a substantially V-shaped cross section. FIG. 15(b) shows a lower press portion 23d in which a plane 23d4 assumes a substantially arcuate cross section. By use of such a plane 23d1 or 23d4, the lower press portion 23d presses the heating member 3 in a direction intersecting the center axis O2 of the hollow portion 2a of the oxygen detection element 2, thereby effectively bringing at least a portion of the heating member 3 into contact with the inner wall surface of the hollow portion 2a of the oxygen detection element 2. FIG. 15(c) shows a lower press portion 23d in which two intersecting planes 23d1 and 23d2 are formed from a single sheet through bending in such a manner as to assume a substantially L-shaped cross section. In FIG. 15(c), the plane 23d1 has a gently curved surface and thus can contact the external circumferential surface of the heating member 3 over a wide region. As a result, even when only the lower press portion 23d is engaged in pressing the heating member 3 in a direction intersecting the center axis O2 of the hollow portion 2a of the oxygen detection element 2, at least a portion of the heating member 3 can be brought into contact with the inner wall surface of the hollow portion 2a of the oxygen detection element 2.

The above-described guide member structures employ the lower press portion 23d, the upper press portion 23e, and the protrusion portion 23f of different shapes. However, these shapes are interchangeable, or one of these shapes may be used as a common shape. Also, any other guide member structures may be employed.

While the invention has been described in detail and with reference to specific embodiments thereof, it will be apparent to one skilled in the art that various changes and modifications can be made therein without departing from the spirit and scope thereof.

This application is based on Japanese Patent Application Nos. Hei. 11-165819 filed Jun. 11, 1999 and 2000-44836 filed Feb. 23, 2000, which are incorporated herein by reference in their entirety.

What is claimed is:

1. An oxygen sensor comprising:

an oxygen detection element assuming the form of a hollow rod which is closed at a front end, and having electrode layers formed on inner and outer surfaces of a hollow portion thereof;

a heating member in the form of a rod disposed within the hollow portion of the oxygen detection element and adapted to heat the oxygen detection element; and a metallic terminal member formed so as to circumferentially surround the heating member and having an attachment portion, which is fixedly attached to an inner surface of the oxygen detection element, directly or indirectly via another member, wherein the metallic terminal member includes at least two press portions located apart from each other in an axial direction of the metallic terminal member, the two press portions elastically pressing the heating member in a direction intersecting a center axis of the hollow portion of the oxygen detection element;

the heating member is held by the metallic terminal member and also by holding means formed separately from the metallic terminal member, and the two press portions cause at least a portion of the heating member to be in contact with an inner wall surface of the hollow portion of the oxygen detection element; and one of the press portions is formed on the attachment portion at an intermediate position between axial ends of the attachment portion, and the one press portion is disposed within an axial length of an engagement between the attachment portion and the inner surface of the oxyoen detection element, the axial length of the engagement extending continuously from a rear-end opening portion of the oxygen detection element.

2. The oxygen sensor as claimed in claim 1, further comprising:

an external cylindrical member for accommodating the oxygen detection element;

a lead wire connected to the metallic terminal member and adapted to lead out an output from an output from the oxygen detection element to an exterior of the oxygen sensor; and a grommet having a lead wire therethrough and fitted into a read-end opening portion of the external cylindrical member, the grommet filling the space between an inner wall of an opening portion of the external cylindrical member and the lead wire to provide a seal;

wherein the holding means comprises a frictional force induced between the grommet and a portion of the lead wire located within the lead wire through-hole.

3. The oxygen sensor as claimed in claim 1, further comprising a ceramic separator having a lead wire through-hole formed therein for passing the lead wire therethrough and disposed on the rear-end portion side of the oxygen detection element, wherein:

the ceramic separator has a heating-member-end-portion accommodation hole formed therein in such a manner as to extend into the ceramic separator from a front end face of the separator; and a bottom surface of the heating-member-end-portion accommodation hole is located at an axially intermediate portion of the ceramic separator and serves as positioning means for the heating member.

4. The oxygen sensor as claimed in claim 1, wherein the press portion formed on the attachment portion is formed such that at least a portion of a circumferential wall of the attachment portion projects radially inward so as to press against an external circumferential surface of the heating member.

5. The oxygen sensor as claimed in claim 1, wherein at least one of the press portions includes an integrally formed guide segment adapted to effect smooth insertion of at least a front end portion of the heating member when the heating member is to be inserted into the metallic terminal member.

6. The oxygen sensor as claimed in claim 1, wherein a portion of a circumferential wall of the attachment portion projects toward an external circumferential surface of the heating member so as to form a protrusion portion, and a location of the protrusion portion determines a location of contact between the heating member and the inner wall surface of the hollow portion of the oxygen detection element.

7. The oxygen sensor as claimed in claim 6,
wherein the attachment portion is inserted directly or indirectly via another member into a counter-bore portion which is formed in the oxygen detection element in such a manner as to extend axially over a predetermined length from an end face of the rear-end opening portion of the hollow portion toward a front end portion of the oxygen detection element, the counter-bore portion having a bore diameter greater than that of the hollow portion; and a position where the protrusion portion presses against the heating member is located on an extension line of the inner wall surface of the hollow portion of the oxygen detection element.

8. The oxygen sensor as claimed in claim 6, wherein the protrusion portion includes an integrally formed guide segment adapted to effect smooth insertion of at least a front end portion of the heating member when the heating member is to be inserted into the metallic terminal member.

9. An oxygen sensor comprising:
an oxygen detection element assuming the form of a hollow rod which is closed at a front end, and having electrode layers formed on inner and outer surfaces of a hollow portion thereof;

a heating member in the form of a rod disposed within the hollow portion of the oxygen detection element and adapted to heat the oxygen detection element; and a metallic terminal member formed so as to circumferentially surround the heating member and having an attachment portion, which is fixedly attached to an inner surface of the oxygen detection element, directly or indirectly via another member, wherein the metallic terminal member includes at least two press portions located apart from each other in an axial direction of the metallic terminal member, the two press portions elastically pressing the heating member in a direction intersecting a center axis of the hollow portion of the oxygen detection element;

the two press portions cause the heating member to extend along and in contact with an inner wall surface of the hollow portion of the oxygen detection element; and one of the press portions is formed on the attachment portion at an intermediate position between axial ends of the attachment portion, and the one press portion is disposed within an axial length of an engagement between the attachment portion and the inner surface of the oxygen detection element, the axial length of the engagement extending continuously from a rear-end opening portion of the oxygen detection element.

10. The oxygen sensor as claimed in claim 9,
further comprising a ceramic separator having a lead wire through-hole formed therein for passing the lead wire therethrough and disposed on the rear-end portion side of the oxygen detection element, wherein:
the ceramic separator has a heating-member-end-portion accommodation hole formed therein in such a manner as to extend into the ceramic separator from a front end face of the separator; and a bottom surface of the heating-member-end-portion accommodation hold is located at an axially intermediate portion of the ceramic separator and serves as positioning means for the heating member.

11. The oxygen sensor as claimed in claim 9, wherein the press portion formed on the attachment portion is formed such that at least a portion of a circumferential wall of the attachment portion projects radially inward so as to press against an external circumferential surface of the heating member.

12. The oxygen sensor as claimed in claim 9, wherein at least one of the press portions includes an integrally formed guide segment adapted to effect smooth insertion of at least a front end portion of the heating member when the heating member is to be inserted into the metallic terminal member.

13. The oxygen sensor as claimed in claim 9, wherein a portion of a circumferential wall of the attachment portion projects toward an external circumferential surface of the heating member so as to form a protrusion portion, and a location of the protrusion portion determines a location of contact between the heating member and the inner wall surface of the hollow portion of the oxygen detection element.

14. The oxygen sensor as claimed in claim 13,
wherein the attachment portion is inserted directly or indirectly via another member into a counter-bore portion which is formed in the oxygen detection element in such a manner as to extend axially over a predetermined length from an end face of the read-end opening portion of the hollow portion toward a front end portion of the oxygen detection element, the counter-bore portion having a bore diameter greater than that of the hollow portion; and a position where the protrusion portion presses against the heating member is located on an extension line of the inner wall surface of the hollow portion of the oxygen detection element.

15. The oxygen sensor as claimed in claim 13, wherein the protrusion portion includes an integrally formed guide segment adapted to effect smooth insertion of at least a front end portion of the heating member when the heating member is to be inserted into the metallic terminal member.

* * * * *